US011288738B1

(12) United States Patent
Samad et al.

(10) Patent No.: US 11,288,738 B1
(45) Date of Patent: Mar. 29, 2022

(54) SYSTEMS AND METHODS FOR STRUCTURING THE FINANCING OF HIGH COST THERAPIES

(71) Applicant: Octaviant Financial, Inc., Metuchen, NJ (US)

(72) Inventors: Emad Samad, Metuchen, NJ (US); John M Nolan, Whitehouse Station, NJ (US); Niles K Chura, Woodbridge, VA (US)

(73) Assignee: Octavian! Financial, Inc., Metuchen, NJ (US)

( * ) Notice: Subject to any disclaimer, the term of this patent is extended or adjusted under 35 U.S.C. 154(b) by 0 days.

(21) Appl. No.: 17/327,604

(22) Filed: May 21, 2021

Related U.S. Application Data

(60) Provisional application No. 63/187,830, filed on May 12, 2021, provisional application No. 63/173,916, filed on Apr. 12, 2021.

(51) Int. Cl.
| | |
|---|---|
| *A61J 1/00* | (2006.01) |
| *G06Q 40/02* | (2012.01) |
| *G16H 10/60* | (2018.01) |
| *G16H 40/20* | (2018.01) |
| *A61K 48/00* | (2006.01) |
| *G16H 70/40* | (2018.01) |
| *G06Q 30/00* | (2012.01) |
| *G06Q 40/08* | (2012.01) |
| *G16H 50/70* | (2018.01) |
| *G16Y 10/50* | (2020.01) |

(52) U.S. Cl.
CPC .............. *G06Q 40/025* (2013.01); *A61J 1/00* (2013.01); *A61K 48/00* (2013.01); *G06Q 30/012* (2013.01); *G06Q 40/08* (2013.01); *G16H 10/60* (2018.01); *G16H 40/20* (2018.01); *G16H 50/70* (2018.01); *G16H 70/40* (2018.01); *B65D 2203/02* (2013.01); *B65D 2585/56* (2013.01); *G16Y 10/50* (2020.01)

(58) Field of Classification Search
CPC .................. B65D 2203/02; B65D 2585/56
USPC ............................................. 206/459.5, 534
See application file for complete search history.

(56) References Cited

U.S. PATENT DOCUMENTS

| 10,046,005 B2 * | 8/2018 | Mousa ................. A61K 31/728 |
| 2002/0123906 A1 | 9/2002 | Goetzke et al. |
| 2002/0194022 A1 | 12/2002 | Comite |

(Continued)

OTHER PUBLICATIONS

ABC News, Child Fights for her life by taking the 'most expensive drug in the world', 11 pages, May 18, 2021.

(Continued)

*Primary Examiner* — Jacob K Ackun
(74) *Attorney, Agent, or Firm* — Choate, Hall & Stewart LLP; William R. Haulbrook; Peter A. Flynn

(57) ABSTRACT

Presented herein are systems and methods for structuring the financing of high cost therapies such as GCTs to address the issues of high-upfront cost (affordability), uncertain durability of the treatment, and portability/transferability of the liability. In certain embodiments, the systems and methods described herein involve a combination of (a) a uniquely-designed, multi-year structured loan that facilitates portability, (b) a performance-based guarantee of efficacy in the form of a value based agreement that may be tied to the tenure of the loan, and (c) securitization of the loan.

13 Claims, 9 Drawing Sheets

(56) References Cited

U.S. PATENT DOCUMENTS

| | | | | |
|---|---|---|---|---|
| 2007/0187266 A1* | 8/2007 | Porter | ............ | G06Q 10/087 206/232 |
| 2008/0103826 A1 | 5/2008 | Barrett | | |
| 2009/0230015 A1* | 9/2009 | Harrison | ............ | G09F 23/00 206/571 |
| 2011/0046985 A1 | 2/2011 | Raheman | | |
| 2011/0120904 A1* | 5/2011 | Harrison | ............ | G09F 23/00 206/528 |
| 2012/0077163 A1* | 3/2012 | Sucar Succar | ............ | A61H 1/00 434/247 |
| 2014/0031757 A1* | 1/2014 | Rozier | ............ | A61M 25/02 604/179 |
| 2014/0060547 A1* | 3/2014 | Vallino | ............ | A61F 5/3761 128/845 |
| 2017/0020783 A1* | 1/2017 | Shani | ............ | B65D 51/1688 |
| 2019/0147141 A9 | 5/2019 | Kahn | | |

OTHER PUBLICATIONS

Cassidy, Bill, How will we pay for the coming generation of potentially curative gene therapies?, 5 pages, Jun. 12, 2019.

Feuerstein, Adam, Bluebird's withdrawal of therapy from Germany could chill talks over gene therapy prices across Europe, 7 pages, Apr. 22, 2021.

Joseph, Andrew, 'It's not a cure': A gene therapy is opening a new chapter for children, but challenges endure, 16 pages, May 25, 2021.

McConaghie, Andrew, Blyvera, the most expensive drug in the world, to be withdrawn after commercial flop, 4 pages, Apr. 20, 2017.

Silverman, Ed, Employers are planning how to blunt the cost of gene therapies, pricey new specialty drugs, 4 pages, Aug. 27, 2020 [retrieved Apr. 9, 2021 from https://www.statnews.com/pharmalot/2020/08/27/employers-gene-therapy-drug-prices-insurance/].

* cited by examiner

SYSTEMS AND METHODS FOR STRUCTURING THE FINANCING OF HIGH COST THERAPIES

CROSS-REFERENCE

This application claims benefit of and priority to U.S. Provisional Application No. 63/173,916 filed Apr. 12, 2021 and U.S. Provisional Application No. 63/187,830 filed May 12, 2021, each of which is entirely incorporated herein by reference for all purposes.

FIELD

This invention relates generally to systems and methods for structuring the financing of high cost therapies (HCTs) in a manner that provides for transferability. More particularly, in certain embodiments, the invention relates to systems and methods for structuring one or more instruments of an HCT financing, where the HCT financing includes a multi-year structured loan, a value based agreement (e.g., a performance agreement, a warranty, or other insurance product), and a securitization.

BACKGROUND

There are an array of challenges associated with expanding the usage of potentially curative high-cost pharmaceuticals, specifically gene and cellular therapies (GCTs) with broad applicability to the entire spectrum of high cost therapies (HCTs). Factors threatening to limit the deployment of these cures include (a) their high cost, (b) uncertainty regarding the efficacy/durability of the therapy, and (c) the potential that beneficiaries will switch employers/insurers.

Examples of these high cost therapies include Zolgensma ($2.1 million one-time cost) manufactured by AveXis, Inc., Zokinvy ($1.0 million/yr) manufactured by Eiger BioPharmaceuticals, Danyelza ($980,000/yr) manufactured by Y-mAbs Therapeutics, Inc., Myalept ($890,000/yr) manufactured by Aegerion Pharmaceuticals, Luxturna ($850,000 one-time cost) manufactured by Spark Therapeutics, Folotyn ($790,000/yr) manufactured by Acrotech Biopharma, Brineura ($730,000/yr) manufactured by BioMarin Pharmaceuticals, Jivi ($720,000/yr) manufactured by Bayer Pharmaceuticals, Inc., Blincyto ($710,000/yr) manufactured by Amgen, Inc., Ravicti ($700,000/yr) manufactured by Horizon Therapeutics, Soliris ($680,000/yr) manufactured by Alexion Pharmaceuticals, Inc., and Abecma ($420,000 one-time cost) manufactured by Bluebird Bio. Zolgensma is a one-time curative therapy to treat children with spinal muscular atrophy. Zokinvy is a treatment for Hutchinson-Gilford progeria syndrome, which costs about $717 per capsule, with patients typically taking four capsules daily. Danyelza is a treatment for patients with neuroblastoma in the bone or bone marrow, which costs about $20,000 per vial, with typical use of 48 vials per year. Myalept is a treatment for generalized lipodystrophy, with typical use being 14 vials per month. Luxturna is a gene therapy that treats a form of retinal dystrophy and is a one-time therapy (one vial administered into each eye). Folotyn is used to treat peripheral T-cell lymphoma, and typical use is 45 vials of the drug per year. Brineura is used to treat a form of Batten disease in pediatric patients, with recommended dosage of 300 mg every two weeks. Jivi is an anti-hemophilic factor therapy for patients with hemophilia A. Blincyto is used to treat a rare form of acute lymphoblastic leukemia, with typical use being about 168 vials per year. Ravicti is used to treat urea cycle disorders, which are genetic conditions that result in high levels of ammonia in the blood; patients are typically given 132 bottles per year at a cost of about $5270 per bottle. Soliris is used to treat certain blood disorders that result in the destruction of red blood cells with recommended dose of about 1200 mg every two weeks. Abecma is a genetically modified autologous T cell immunotherapy for treatment of adult patients with relapsed or refractory multiple myeloma, administered as a one-time infusion. Some of these drugs can be self-administered and others must be administered by a healthcare provider.

Of particular interest, and challenge with respect to financing, are one-time dose high cost GCT drugs. As the number of such GCTs approved by the US Food and Drug Administration (FDA) to treat orphan and prevalent indications increases over the next decade, the economic burden placed on health benefit payers will grow substantially, as the costs of these therapies can exceed $2 million for the one-time dose. The initial burden is likely to be greatest amongst middle market self-insurers with covered beneficiaries who would benefit from the administration of a GCT. Unlike many large, well-capitalized companies with hundreds—if not thousands—of beneficiaries, these smaller entities are often insufficiently capitalized to handle a substantial near-term disbursement. Even with the assistance of stop-loss protection or reinsurance, the triggering of those policies typically results in a material premium increase to the self-insurer in addition to the lasering of the GCT beneficiary from the policy, rendering the self-insurer exposed to any and all future healthcare costs incurred by that individual.

In addition to the elevated cost, there is also no guarantee that a GCT will be effective in every individual to whom it is administered. Current failure rates for the few commercialized and late development stage GCTs can be high. Further, visibility regarding durability (i.e. how long the treatment benefit will last) may be poor even for those therapies which are deemed to be clinically efficacious in the short term. Payers will incur liabilities for therapies that may ultimately not alleviate the burden of disease. In the event a GCT fails, many beneficiaries will resort back to high cost standards of care, the cost of which will still be borne by the payer who now has taken on the additional liability of a failed GCT.

Beyond cost and uncertain durability, all payers, even larger, well-capitalized self-insurers, will be exposed to risk if a GCT-treated beneficiary departs from their health plan. In such circumstances, payers may continue to pay for a GCT only to have that covered beneficiary leave the plan because of a change in employment. In such circumstances, the payer has incurred an inordinate portion of the liability for the beneficiary's treatment. This transferability risk highlights the economic timing mismatch between a large expense borne by the payer and future revenue streams (i.e., premium payments) and health benefits.

In short, the cost of GCTs creates a potentially untenable situation for many payers and may hinder their ability to provide benefits to all covered beneficiaries on a go-forward basis. This will become of greater concern as GCTs proliferate over the next years.

SUMMARY

Presented herein are systems and methods for structuring the financing of high cost therapies such as GCTs to address the issues of high-upfront cost (affordability), uncertain durability of the treatment, and portability/transferability of the liability. In certain embodiments, the systems and methods described herein involve a combination of (a) a uniquely-designed, multi-year structured loan that facilitates portability, (b) a performance-based guarantee of efficacy in the form of a warranty that may be tied to the tenure of the loan, and (c) securitization of the loan.

Loan

In certain embodiments, the loan provides a mechanism by which payers can spread the cost of GCTs over time through manageable periodic principal and interest payments. Extending the payment period in this manner more appropriately matches the expense with both the presumed benefits of the therapy and the premium streams received by payers.

Although various embodiments of the loan described herein provide a degree of standardization, the terms are flexible enough to address peculiarities of the covered therapeutic and can be modified based on needs of both the borrower and manufacturer. Terms may be calculated utilizing various stochastic, algorithmic, and/or machine learning (and/or other forms of artificial intelligence (AI)) methodologies which utilize inputs including, but not limited to, one or more of the following: the total cost of the therapy (inclusive of service and administration costs), the credit rating of the borrower, the current debt service of the borrower, the ability of the borrowing firm to collateralize the loan, the financial solvency and cash flow generating capability of the borrowing firm, the desire of the manufacturer to provide subvention, the amount, if any, of the manufacturer holdback, the projected efficacy of the GCT, the nature, cost and terms of an associated warranty, the duration of the warranty, the existence, if any, and cost of a current, non-GCT or GCT standard of care therapy, the level of interest rate benchmarks such as LIBOR (London Interbank Offered Rate) for variable rate loans, prevailing market interest rates for loans of similar tenor and risk profile, market-wide default rates, the existence, if any, of prepayment penalties, the size of any upfront draws and other metrics deemed necessary by the lender.

In certain embodiments, the principal amount of the loan will include an upfront draw that is equivalent to a percentage of the cost of the GCT plus the associated value based agreement (VBA) premium (e.g., performance agreement, warranty, or other insurance product premium), initial outcomes benefit administrator (OBA) fees, certain approved costs and expenses of pre-therapy therapeutic treatments and services, procedure-related costs, and an arrangement fee. The size of this upfront draw may be calculated so as to not trigger any best-price and anti-kickback features of federal, state, local, and/or other applicable law. In certain embodiments, the lender can work with HCT (e.g., GCT) manufacturers to apply for a unique National Drug Code (NDC) that not only uniquely identifies the GCT, but also the mechanism of payment through the HCT financing structure. The mechanism of financing may be described or otherwise referenced in the packaging of the drug, for example. While the NDC coding scheme does not directly code for payment mechanism, a unique NDC can be created for various packaging constructs of the GCT. For example, if such construct is solely sold through distribution channels in which the HCT financing structure is utilized as the payment mechanism, the NDC, ipso facto, is tied to the HCT financing structure.

In certain embodiments, a determination period is established in conjunction with the payer and GCT manufacturer (e.g., two weeks or other time period following the administration of the GCT) to assess whether the therapy has successfully been transfected into the patient/beneficiary or whether it has generated an adverse response which would render the therapy ineffective or undesired. If the administration is determined by the OBA to be indicatively successful, a second draw totaling the remainder of the loan value minus a predetermined manufacturer holdback will be paid. At this point, the loan will be considered seasoned and the borrower will commence making periodic installments of principal and interest repayment. If, however, the administration of the therapy is assessed to be unsuccessful during the determination period, the warranty will be triggered and the payout of the warranty will be used to compensate the lender for any upfront draw that has been paid and any prepayment penalty associated with early termination of the loan.

In certain embodiments, a contractually defined "episode of care" is set to match the instrument's tenor. In certain embodiments, the episode of care will begin when the patient/beneficiary is prescribed the therapy, or at the execution of the term sheet or loan documents, or at another point in time decided upon by the lender and key stakeholders (e.g., the payer, manufacturer, etc.). The episode of care will continue forward as the patient/beneficiary continues to be monitored by an external OBA to assess whether the GCT is providing the efficacy contractually agreed to by the manufacturer, as expressed by the terms of the warranty, and during which the loan recipient is continuing to make periodic payments of principal and interest. As such, the episode of care also includes post-therapeutic treatments and services, as recommended by the manufacturer and agreed to by the payer for monitoring and supporting the patient/beneficiary. The total cost of the loan could cover not only the cost of the therapeutic itself, but also the pre- and post-therapeutic health care costs associated with the indication and GCT therapy, such as healthcare professional visits, medical tests and scans, and other healthcare costs related to the patient/beneficiary diagnosis and/or therapeutic. During the episode of care, the diagnosis of the patient/beneficiary is considered to be unchanged. This determination of the episode of care as part of the loan term structure is crucial to the notion of portability of the HCT financing structure. Defining the episode of care establishes a pre-existing condition, which is a key component of the Affordable Healthcare Act.

Warranty or Other Value Based Agreement (VBA)

To mitigate the risk of GCT therapy faced by payers and to offset the loan liability in the event of therapeutic inefficacy, in certain embodiments, the HCT financing also includes a performance guarantee in the form of a lender's warranty, a manufacturer supplied warranty, or other value based agreement (VBA), or third-party supplied warranty or VBA ("warranty"). In certain embodiments, the warranty is structured to guarantee the efficacy of GCT therapy using predefined, measurable, reproducible and verifiable criteria (serum biomarkers, functional tests, etc.) agreed to by both the manufacturer and payer/self-insurer in advance of the administration of the GCT. These measures, which will be assessed periodically by a third-party outcomes-based administrator (OBA), constitute the criteria by which the GCT will be considered effective. If a therapy is assessed as ineffective during the period in which the warranty is active, the warranty will be triggered and the payer will receive a disbursement as stipulated under the terms of the warranty. In most cases, the disbursement can be used to directly compensate the payer for any remaining loan liability, which may include compensation for the upfront draw and the prepayment penalty; however, the warranty disbursement may also be used to cover an equivalent value (of the remaining loan liability) in costs incurred by the payer in reverting the covered patient/beneficiary to standard of care therapy (payment in kind).

The lender may work in conjunction with third party insurers to provide the warranty or it may work directly with manufacturers to establish the necessary corporate and regulatory structures that are required to implement a successful warranty program that does not infringe upon CMS Best Price (Centers for Medicare and Medicaid Services Best Price). In such instances where the GCT manufacturer chooses to directly issue the warranty, the lender, or an associated designee of the lender, will assist the manufacturer in developing warranty terms that are based both on the therapeutic performance of the GCT in clinical and post-marketing trials and which are deemed likely to maximize demand interest in the market. Like the loan, the term structure of the warranty can be calculated utilizing various stochastic, algorithmic and artificial intelligence (AI) methodologies which utilize inputs including, but not limited to, one or more of the following: the availability of relevant efficacy data provided by the manufacturer, the risk tolerance of the manufacturer, the cost of the GCT, the availability, if any, and cost of a standard of care alternative therapy, the prevalence of the disease, payer survey data, and any other inputs deemed necessary by both the lender and the manufacturer.

In certain embodiments in which the warranty is manufacturer-issued, the lender, or its designee, can work with the manufacturer to create and structure an incorporated cell captive—if one does not already exist—a legal subsidiary entity to which the warranty can be transferred in exchange for a premium and the receipt of a contractual liability insurance policy. The cell captive may be required to have risk-based capital ratios commensurate to the level of risk assumed in combination of cash and lines of credit. The cell captive can subsequently enter into an agreement with a managing general underwriter selected by the manufacturer in consultation with the lender to run the insurance operations of the captive. The captive may, at its discretion, purchase reinsurance to spread the risk of non-efficacy to the broader market. The lender may at some future time work with a third-party insurance underwriter to whom the manufacturer can directly transfer the warranty liability for a premium. The underwriter may require the manufacturer to contribute to a risk pool that will be utilized to pay claims on warranties that have been triggered by the inefficacy of their product.

In certain embodiments, a third-party outcomes-based administrator (OBA), selected with the consent of the payer and GCT manufacturer, regularly monitors (e.g., at predetermined times, specific to the GCT) the patient/beneficiary according to the terms stipulated by the warranty to access GCT efficacy. The OBA adjudicates whether the payout terms of the warranty have been triggered and, if so, direct the liable party to make disbursements as stipulated. Warranties are structured so as to permit transfer to another party in the event that the patient/beneficiary is transferred to another payer.

Securitization

In certain embodiments, once a sufficient HCT financing loan portfolio has been created (with "sufficiency" defined, for example, in terms of the risk profile and diversity of the borrowers, the diversity of GCTs covered, the diversity of GCT manufacturers, in addition to other metrics), the lender will bundle these loans for the purposes of securitization and distribution to the broader financial markets. For example, the securitization basket may comprise 200-300 HCT financing loans with a notional value of 300 MM-500 MM USD. Credit rating, average coupon, position sizing, and the like, can be determined at the time of creation. Tranching of the loan cash flows can be determined during the creation of the securitization and subject to various market conditions that would affect the attractiveness of the securities to the market. Loans associated with multiple GCTs, various payer types, differing loan tenors, and the like, may be ideal to achieve the maximum diversification benefit from the total portfolio and to reduce the risk profile of both the overall loan basket as well as the individual tranches.

In certain embodiments, the process of securitization provides a mechanism to offboard risk of the HCT financing to the market and facilitates potentially lower interest rates for individual loans to payers/borrowers.

It is believed the proposed HCT financing payment solution for GCTs provided herein is the first to combine a multi-year structure loan, a warranty, and a securitization. It is also believed that the proposed solution described herein is the first to contractually link the term structure of the financial instrument with the episode of care, thereby establishing and/or defining a pre-existing condition, rendering transferability possible. While embodiments are described herein primarily with respect to GCTs (e.g., therapies that involve administration of a one-time dose drug to a beneficiary), it is contemplated that the systems, processes, and description provided herein may be applied more generally to the financing of other high cost therapies.

In one aspect, the invention is directed to a method for assessment, by a lender (e.g., a senior lender), of an application for an instrument (e.g., a multi-year structured loan and/or a warranty), and upon approval, for determination of one or more terms of the instrument, for financing one or more of (i), (ii), and (iii) as follows (collectively, the HCT financing): (i) a high cost therapy (HCT) [e.g., a gene or cell therapy (GCT), e.g., said HCT comprising a high-cost treatment, e.g., a GCT drug, e.g., a single or finite dose gene therapy, e.g., a single or finite dose cellular therapy, e.g., wherein the high cost therapy has a cost of at least 100,000 USD, e.g., at least 200,000 USD, e.g., at least 300,000 USD] to be administered to a HCT beneficiary (e.g., a person covered under a health insurance policy, e.g., a health insurance policy of an employer-sponsored health plan, e.g., a health insurance policy provided by a self-insured employer group (SIEG) or its agent) [e.g., wherein the financing of the HCT comprises one or more of an upfront draw (e.g., a first senior unsecured term loan), a second draw (e.g., a second senior unsecured term loan), and a holdback amount (e.g., an amount made available to a borrower by a manufacturer of the HCT)], (ii) bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary [e.g., wherein the financing of the bundled expenses comprises a delayed draw], and (iii) an associated performance-based guaranty of the (e.g., at least initial) efficacy of the HCT administered to the HCT beneficiary [e.g., said guaranty in the form of a warranty or other value based agreement (VBA)], wherein said instrument is structured in a manner to facilitate portability (e.g., transferability) of said instrument (e.g., transfer of liability from the borrower to a subsequent payer) over the tenor of the instrument, the method comprising: (a) receiving (e.g., by a processor of a computing platform of the lender) a first set of data of the application for the instrument, said application having been transmitted to the lender by a borrower (e.g., the SIEG or its agent); and (b) determining (e.g., by the processor) whether the instrument is approved using the first set of data and/or (e.g., upon approval) determining [e.g., by the processor, e.g., said processor utilizing stochastic and/or algorithmic and/or machine learning (and/or other forms of artificial intelligence (AI)) methodologies] a structure (e.g., one or more terms) of the instrument such that one or more of (i) to (vi) applies, as follows: (i) said HCT financing comprises an upfront draw paid to a party [e.g., a specialty pharmacy; e.g., a treatment facility (hospital, outpatient clinic); e.g., a pharmaceutical manufacturer] that provides and/or administers the HCT to the HCT beneficiary [e.g., wherein said upfront draw is at least 30% (e.g., at least 40%, at least 50%, at least 60%, at least 70%, or about 77%) of the cost of the HCT (e.g., plus procedure-related costs and/or VBA premium cost and/or initial outcomes benefit administrator (OBA) fee and/or pre-therapeutic bundled expenses and/or an arrangement fee)] and is made at or near the time of administration of the HCT to the HCT beneficiary (e.g., just prior to or after the therapy); (ii) said HCT financing comprises a premium payment for a value based agreement (VBA) (e.g., a performance agreement, a warranty, or other insurance product) structured as a performance guaranty of initial efficacy of the HCT for the HCT beneficiary [e.g., wherein said initial efficacy is determined using predefined, measurable, reproducible and/or verifiable criteria (e.g., serum biomarkers, functional tests, etc.), e.g., wherein said criteria are agreed to by both the manufacturer of the HCT (e.g., the manufacturer of the GCT drug) and the lender or an identified outcomes benefit administrator (OBA) in advance of administration of the therapy (e.g., the GCT drug) to the HCT beneficiary]; (iii) said HCT financing comprises a second draw paid within an agreed-upon period of time after administration of the HCT and upon determination (e.g., by an identified OBA) of initial efficacy of the HCT for the HCT beneficiary [e.g., wherein said second draw covers the remainder of the cost of the HCT (e.g., plus an estimate of post-therapeutic bundled expenses and/or anticipated remaining outcomes benefit administrator (OBA) fees), or covers said remainder minus a manufacturer's holdback amount (e.g., 5-25%, e.g., 10%, of the cost of the HCT)]; (iv) said HCT financing comprises bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary, said bundled expenses being compensated for a contractually-defined episode of care, wherein said episode of care is a time period associated with the HCT for which a bundled payment (e.g., condition-specific capitation) is made (e.g., wherein said episode of care is contractually defined as a time period beginning when the HCT is prescribed to the HCT beneficiary and lasting until maturity of the instrument, e.g., the loan and/or the guaranty); (v) said HCT financing comprises a multi-year structured loan having a tenor that ends contiguously with a defined episode of care, wherein said episode of care is contractually defined to establish a pre-existing condition of the HCT beneficiary, thereby facilitating portability and/or transferability of associated liability from the borrower (e.g., the SIEG or its agent) to another party [e.g., in the event of (and upon) exit of the policyholder from the borrower's health plan and upon subsequent entry of the (now former) policyholder under a new health plan covering the HCT beneficiary)] while the HCT beneficiary is considered to have the pre-existing condition; and (vi) said HCT financing comprises a value based agreement (e.g., a performance agreement, a warranty, or other insurance product) having a period (e.g., warranty period) that ends contiguously with a defined episode of care, wherein said episode of care is contractually defined to establish a pre-existing condition of the HCT beneficiary, thereby facilitating portability and/or transferability of associated liability [e.g., in the event of (and upon) exit of the policyholder from the borrower's health plan (e.g., and upon subsequent entry of the (now former) policyholder under a new health plan covering the HCT beneficiary)] while the HCT beneficiary is considered to have the pre-existing condition.

In certain embodiments, the method further comprises: (c) identifying (e.g., by the processor, e.g., automatically identifying, by the processor of the computing platform) a bundle of HCT loans (e.g., including the loan of the HCT financing of claim 1) to include in a securitization basket and determining (e.g., by the processor) one or more terms (e.g., a credit rating, average coupon, position sizing, tranching etc.) of the securitization basket (e.g., thereby providing a mechanism to offboard risk to a broader market and/or to facilitate potentially lower interest rates for individual loans to borrowers, e.g., SIEGs).

In certain embodiments, the high-cost initial treatment is a drug (e.g., GCT drug) having a National Drug Code (NDC) that identifies mechanism of payment via the HCT financing (e.g., wherein said NDC denotes drug packaging that links to said mechanism of payment).

In certain embodiments, step (b) comprises determining (e.g., by the processor) the structure of the instrument, wherein the instrument is a multi-year structured loan having a tenor that matches said episode of care, and wherein the loan comprises: an upfront draw to be paid upon administration of the high-cost initial treatment to the HCT beneficiary (e.g., wherein the upfront draw is an amount in a range from 50% to 90% of the cost of the initial treatment which may or may not include associated services that follow such initial treatment that are bundled together with the cost of the initial treatment), and a second, subsequent payment to be made upon a final close of the loan following and contingent upon a determination of initial efficacy of the HCT for the HCT beneficiary.

In certain embodiments, the final close is in an amount that covers the remainder of the cost of the HCT, which may or may not include the associated services, less a holdback (e.g., 5%-25%, e.g., 10% of the cost of the HCT) to be paid by borrower to the manufacturer of the high cost initial treatment, e.g., at maturity of the loan. In certain embodiments, the loan comprises a senior tranche amortization period, and wherein the holdback is subordinate to the senior tranche (e.g., the holdback is paid only when the senior tranche is paid in full).

In certain embodiments, the warranty pays off the upfront draw (e.g., plus a prepayment penalty) upon a determination of initial non-efficacy of the initial treatment in the HCT beneficiary.

In certain embodiments, step (b) comprises determining (e.g., by the processor) a structure (e.g., one or more terms) of the instrument of the HCT financing based on one or more of the following: total cost of the HCT (e.g., exclusive or inclusive of service and administration costs); credit rating of the borrower; current debt service of the borrower; assessment of ability of the borrowing firm to collateralize the loan; assessment of financial solvency and cash flow generating capability of the borrowing firm; assessment of desire of the manufacturer to provide subvention; amount, if any, of manufacturer holdback; projected efficacy of the HCT; nature, cost and terms of an associated warranty; duration of the warranty; the existence, if any, and cost of a current, non-HCT or HCT standard of care therapy; level of interest rate benchmarks such as LIBOR (London Interbank Offered Rate) for variable rate loans; prevailing market interest rates for loans of similar tenor and risk profile; market-wide default rates; existence, if any, of prepayment penalties; and size of any upfront draws.

In another aspect, the invention is directed to a packaged pharmaceutical composition [[alternatively, a kit]] comprising a pharmaceutically acceptable vessel, a therapeutic agent secured [[alternatively, sealed]] within the vessel, and a label [[alternatively, package label or vessel label]] [e.g., wherein the pharmaceutically acceptable vessel comprises a vial (e.g., a cryovial or other vial), tube (e.g., a test tube or other tube), multi-well plate, ampule, bottle, bag, box, pouch, patch, syringe, blister pack, strip pack, sealed foil, cell culture bag, intravenous (IV) solution bag, cryobag, vitrification straw, drug delivery device, or other pharmaceutically acceptable vessel known in the art], wherein the therapeutic agent comprises a high cost therapy drug (a HCT drug), and the label comprises a description and/or code (e.g., NDC) that identifies (e.g., a code that is linked to a description of) how the HCT drug is financed (e.g., the HCT financing).

In certain embodiments, the description on the label indicates one or more of (i) to (vi) is applicable to said HCT financing, as follows: (i) said HCT financing comprises an upfront draw paid to a party [e.g., a specialty pharmacy; e.g., a treatment facility (hospital, outpatient clinic); e.g., a pharmaceutical manufacturer] that provides and/or administers the HCT to the HCT beneficiary [e.g., wherein said upfront draw is at least 30% (e.g., at least 40%, at least 50%, at least 60%, at least 70%, or about 77%) of the cost of the HCT (e.g., plus procedure-related costs and/or VBA premium cost and/or initial outcomes benefit administrator (OBA) fee and/or pre-therapeutic bundled expenses and/or an arrangement fee)] and is made at or near the time of administration of the HCT to the HCT beneficiary (e.g., just prior to or after the therapy); (ii) said HCT financing comprises a premium payment for a value based agreement (VBA) (e.g., a performance agreement, a warranty, or other insurance product) structured as a performance guaranty of initial efficacy of the HCT for the HCT beneficiary [e.g., wherein said initial efficacy is determined using predefined, measurable, reproducible and/or verifiable criteria (e.g., serum biomarkers, functional tests, etc.), e.g., wherein said criteria are agreed to by both the manufacturer of the HCT (e.g., the manufacturer of the GCT drug) and the lender or an identified outcomes benefit administrator (OBA) in advance of administration of the therapy (e.g., the GCT drug) to the HCT beneficiary]; (iii) said HCT financing comprises a second draw paid within an agreed-upon period of time after administration of the HCT and upon determination (e.g., by an identified OBA) of initial efficacy of the HCT for the HCT beneficiary [e.g., wherein said second draw covers the remainder of the cost of the HCT (e.g., plus an estimate of post-therapeutic bundled expenses and/or anticipated remaining outcomes benefit administrator (OBA) fees), or covers said remainder minus a manufacturer's holdback amount (e.g., 5-25%, e.g., 10%, of the cost of the HCT)]; (iv) said HCT financing comprises bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary, said bundled expenses being compensated for a contractually-defined episode of care, wherein said episode of care is a time period associated with the HCT for which a bundled payment (e.g., condition-specific capitation) is made (e.g., wherein said episode of care is contractually defined as a time period beginning when the HCT is prescribed to the HCT beneficiary and lasting until maturity of the instrument, e.g., the loan and/or the guaranty); (v) said HCT financing comprises a multi-year structured loan having a tenor that ends contiguously with a defined episode of care, wherein said episode of care is contractually defined to establish a pre-existing condition of the HCT beneficiary, thereby facilitating portability and/or transferability of associated liability from the borrower (e.g., an SIEG or its agent) to another party [e.g., in the event of (and upon) exit of the policyholder from the borrower's health plan (e.g., and upon subsequent entry of the (now former) policyholder under a new health plan covering the HCT beneficiary)] while the HCT beneficiary is considered to have the pre-existing condition; and (vi) said HCT financing comprises a value based agreement (e.g., a performance agreement, a warranty, or other insurance product) having a period (e.g., warranty period) that ends contiguously with a defined episode of care, wherein said episode of care is contractually defined to establish a pre-existing condition of the HCT beneficiary, thereby facilitating portability and/or transferability of associated liability [e.g., in the event of (and upon) exit of the policyholder from the borrower's health plan (e.g., and upon subsequent entry of the (now former) policyholder under a new health plan covering the HCT beneficiary)] while the HCT beneficiary is considered to have the pre-existing condition.

In certain embodiments, the drug is a gene or cell therapy drug (GCT drug).

In certain embodiments, the drug is a single or finite dose gene and/or cellular therapy.

In certain embodiments, the drug comprises one or more members selected from the group consisting of: a biologic drug, a small molecule drug, a gene therapy, and a cell therapy (e.g., CAR T-cell therapy). In certain embodiments, the drug comprises one or more members selected from the group consisting of: an excipient or other pharmaceutically acceptable carrier, In certain embodiments, the pharmaceutically acceptable vessel contains a unit dose of the therapeutic agent.

In one or more additional aspects, the invention is directed to a system for assessment of an application for an instrument (e.g., a loan and/or a warranty), and upon approval, for determination of one or more terms of the instrument that forms part of an HCT financing, the system comprising: a processor of a computing device (e.g., an enterprise system); and a memory having instructions stored thereon, wherein the instructions, when executed by the processor, cause the processor to perform the method of any one of the aspects and embodiments described herein.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which.

Figure 1:
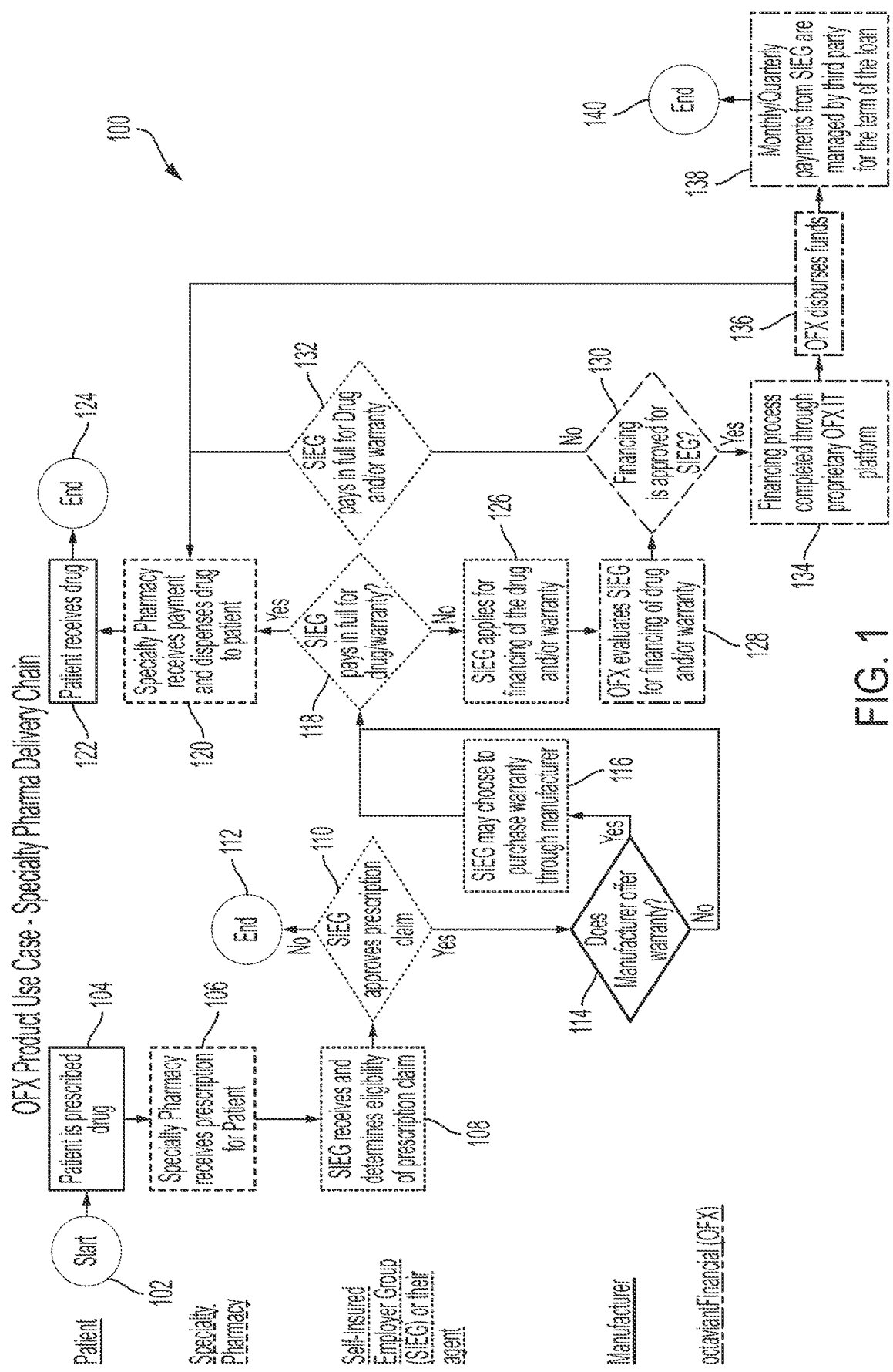
FIG. 1 is a block flow diagram showing the process for financing of a HCT drug administered to a HCT beneficiary, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Agent: As used herein, the term "agent" may refer to any chemical entity, including without limitation any of one or more of an atom, molecule, compound, amino acid, polypeptide, nucleotide, nucleic acid, protein, protein complex, liquid, solution, saccharide, polysaccharide, lipid, or combination or complex thereof.

Antibody: As used herein, the term "antibody" refers to a polypeptide that includes one or more canonical immunoglobulin sequence elements sufficient to confer specific binding to a particular antigen (e.g., a heavy chain variable domain, a light chain variable domain, and/or one or more CDRs). Thus, the term antibody includes, without limitation, human antibodies, non-human antibodies, synthetic and/or engineered antibodies, fragments thereof, and agents including the same. Antibodies can be naturally occurring immunoglobulins (e.g., generated by an organism reacting to an antigen). Synthetic, non-naturally occurring, or engineered antibodies can be produced by recombinant engineering, chemical synthesis, or other artificial systems or methodologies known to those of skill in the art.

As is known in the art, typical human immunoglobulins are approximately 150 kD tetrameric agents that include two identical heavy (H) chain polypeptides (about 50 kD each) and two identical light (L) chain polypeptides (about 25 kD each) that associate with each other to form a structure commonly referred to as a "Y-shaped" structure. Typically, each heavy chain includes a heavy chain variable domain (VH) and a heavy chain constant domain (CH). The heavy chain constant domain includes three CH domains: CH1, CH2 and CH3. A short region, known as the "switch", connects the heavy chain variable and constant regions. The "hinge" connects CH2 and CH3 domains to the rest of the immunoglobulin. Each light chain includes a light chain variable domain (VL) and a light chain constant domain (CL), separated from one another by another "switch." Each variable domain contains three hypervariable loops known as "complement determining regions" (CDR1, CDR2, and CDR3) and four somewhat invariant "framework" regions (FR1, FR2, FR3, and FR4). In each VH and VL, the three CDRs and four FRs are arranged from amino-terminus to carboxy-terminus in the following order: FR1, CDR1, FR2, CDR2, FR3, CDR3, and FR4. The variable regions of a heavy and/or a light chain are typically understood to provide a binding moiety that can interact with an antigen. Constant domains can mediate binding of an antibody to various immune system cells (e.g., effector cells and/or cells that mediate cytotoxicity), receptors, and elements of the complement system. Heavy and light chains are linked to one another by a single disulfide bond, and two other disulfide bonds connect the heavy chain hinge regions to one another, so that the dimers are connected to one another and the tetramer is formed. When natural immunoglobulins fold, the FR regions form the beta sheets that provide the structural framework for the domains, and the CDR loop regions from both the heavy and light chains are brought together in three-dimensional space so that they create a single hypervariable antigen binding site located at the tip of the Y structure.

In some embodiments, an antibody is a polyclonal, monoclonal, monospecific, or multispecific antibody (e.g., a bispecific antibody). In some embodiments, an antibody includes at least one light chain monomer or dimer, at least one heavy chain monomer or dimer, at least one heavy chain-light chain dimer, or a tetramer that includes two heavy chain monomers and two light chain monomers. Moreover, the term "antibody" can include (unless otherwise stated or clear from context) any art-known constructs or formats utilizing antibody structural and/or functional features including without limitation intrabodies, domain antibodies, antibody mimetics, Zybodies®, Fab fragments, Fab' fragments, F(ab')2 fragments, Fd' fragments, Fd fragments, isolated CDRs or sets thereof, single chain antibodies, single-chain Fvs (scFvs), disulfide-linked Fvs (sdFv), polypeptide-Fc fusions, single domain antibodies (e.g., shark single domain antibodies such as IgNAR or fragments thereof), cameloid antibodies, camelized antibodies, masked antibodies (e.g., Probodies®), affybodies, anti-idiotypic (anti-Id) antibodies (including, e.g., anti-anti-Id antibodies), Small Modular ImmunoPharmaceuticals ("SMIPs™"), single chain or Tandem diabodies (TandAb®), VHHs, Anticalins®, Nanobodies® minibodies, BiTE®s, ankyrin repeat proteins or DARPINs®, Avimers®, DARTs, TCR-like antibodies, Adnectins®, Affilins®, Trans-Bodies®, Affibodies®, TrimerX®, MicroProteins, Fynomers®, Centyrins®, and KALBITOR®s, CARs, engineered TCRs, and antigen-binding fragments of any of the above.

In various embodiments, an antibody includes one or more structural elements recognized by those skilled in the art as a complementarity determining region (CDR) or variable domain. In some embodiments, an antibody can be a covalently modified ("conjugated") antibody (e.g., an antibody that includes a polypeptide including one or more canonical immunoglobulin sequence elements sufficient to confer specific binding to a particular antigen, where the polypeptide is covalently linked with one or more of a therapeutic agent, a detectable moiety, another polypeptide, a glycan, or a polyethylene glycol molecule). In some embodiments, antibody sequence elements are humanized, primatized, chimeric, etc, as is known in the art.

An antibody including a heavy chain constant domain can be, without limitation, an antibody of any known class, including but not limited to, IgA, secretory IgA, IgG, IgE and IgM, based on heavy chain constant domain amino acid sequence (e.g., alpha (α), delta (δ), epsilon (ε), gamma (γ) and mu (μ)). IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. As used herein, a "light chain" can be of a distinct type, e.g., kappa (κ) or lambda (λ), based on the amino acid sequence of the light chain constant domain. In some embodiments, an antibody has constant region sequences that are characteristic of mouse, rabbit, primate, or human immunoglobulins. Naturally-produced immunoglobulins are glycosylated, typically on the CH2 domain. As is known in the art, affinity and/or other binding attributes of Fc regions for Fc receptors can be modulated through glycosylation or other modification. In some embodiments, an antibody may lack a covalent modification (e.g., attachment of a glycan) that it would have if produced naturally. In some embodiments, antibodies produced and/or utilized in accordance with the present invention include glycosylated Fc domains, including Fc domains with modified or engineered such glycosylation.

Antibody fragment: As used herein, an "antibody fragment" refers to a portion of an antibody as described herein, and typically refers to a portion that includes an antigen-binding portion or variable region thereof. An antibody fragment can be produced by any means. For example, in some embodiments, an antibody fragment can be enzymatically or chemically produced by fragmentation of an intact antibody. Alternatively, in some embodiments, an antibody fragment can be recombinantly produced (i.e., by expression of an engineered nucleic acid sequence. In some embodiments, an antibody fragment can be wholly or partially synthetically produced. In some embodiments, an antibody fragment (particularly an antigen-binding antibody fragment) can have a length of at least about 50, 60, 70, 80, 90, 100, 110, 120, 130, 140, 150, 160, 170, 180, 190 amino acids or more, in some embodiments at least about 200 amino acids.

Biologic drug or biological product: As used herein, the terms "biologic drug" or "biological product" refers to a therapeutic agent that is or includes one or more of a virus, antibody, antibody fragment, nucleic acid (e.g., DNA or RNA), polypeptide, vaccine, cell, bodily fluid (e.g., blood), bodily fluid component, serum, allergenic agent, toxin, antitoxin, and/or a trivalent organic arsenic compound, and/or analogous products and derivatives thereof. In various embodiments, a biologic drug can be produced according to a process that includes a virus or living cell. In certain embodiments, a unit dose of a biologic drug can be characterized in that the unit dose can include molecules of the biological drug that are non-identical, e.g., that include slight variation resulting from the process of production. In various embodiments, a biologic drug can be synthesized, e.g., chemically synthesized and/or synthesized without use of a virus or cell. In various embodiments, a biologic drug is not a small molecule. In certain particular embodiments, a biologic drug or biological product means a virus, therapeutic serum, toxin, antitoxin, vaccine, blood, blood component or derivative, allergenic product, protein, or analogous product, or arsphenamine or derivative of arsphenamine (or any other trivalent organic arsenic compound), applicable to the prevention, treatment, or cure of a disease or condition of human beings.

CAR T-cell or CAR-T therapy: As used herein "CAR T-cell therapy" or "CAR-T therapy" refers to the use of T cells (autologous or allogeneic) engineered with chimeric antigen receptors (CARs, also known as chimeric immuno-receptors, chimeric T cell receptors, or artificial T cell receptors) as a therapeutic agent in the treatment of a disease, for example, cancer.

Excipient: As used herein, "excipient" refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

Gene therapy: As used herein, the term "gene therapy" refers to the introduction of genetic material into cells to make a beneficial protein and/or otherwise compensate for abnormal genes, for example, in the treatment of a genetic disorder. The genetic material may be introduced into cells of a subject, for example, using a viral vector, naked DNA, or other technique. In certain embodiments, the expression of the gene is suppressed. In certain embodiments, the expression of the gene is enhanced. In certain embodiments, the temporal or spatial pattern of the expression of the gene is modulated.

Naked DNA: As used herein, the term "naked DNA" refers to DNA that is not associated with proteins, lipids, or other molecules to protect it. Administration of naked DNA to a subject (e.g., via intramuscular injection) has been used in gene therapy as a non-viral transfection method.

Nucleic acid: As used herein, in its broadest sense, the term "nucleic acid" refers to any compound and/or substance that is, or can be incorporated into, an oligonucleotide chain. In some embodiments, the term nucleic acid refers to an individual nucleic acid residue (e.g., a nucleotide and/or nucleoside), and in some embodiments refers to an polynucleotide chain including a plurality of individual nucleic acid residues. A nucleic acid can be or include genetic material, for example, DNA, RNA, or a combinations thereof. A nucleic acid can include natural nucleic acid residues, nucleic acid analogs, and/or synthetic residues. In some embodiments, a nucleic acid includes natural nucleotides (e.g., adenosine, thymidine, guanosine, cytidine, and/or uridine). In some embodiments, a nucleic acid is or includes of one or more nucleotide analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid has a nucleotide sequence that encodes a functional gene product such as an RNA or polypeptide. In some embodiments, a nucleic acid includes one or more introns. In some embodiments, a nucleic acid includes one or more genes. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid analog differs from a nucleic acid in that it does not utilize a phosphodiester backbone. For example, in some embodiments, a nucleic acid can include one or more peptide nucleic acids, which are known in the art and have peptide bonds instead of phosphodiester bonds in the backbone. Alternatively or additionally, in some embodiments, a nucleic acid has one or more phosphorothioate and/or 5'-N-phosphoramidite linkages rather than phosphodiester bonds. In some embodiments, a nucleic acid includes one or more modified sugars (e.g., 2'-fluororibose, ribose, 2'-deoxyribose, arabinose, and hexose) as compared with natural nucleic acids. In some embodiments, a nucleic acid can include at least 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 400, 500, 600, 700, 800, 900, 1000, 1500, 2000, 2500, 3000, 3500, 4000, 4500, 5000 or more residues. In some embodiments, a nucleic acid is partly or wholly single stranded, or partly or wholly double stranded. In some embodiments, a nucleic acid has enzymatic activity.

Pharmaceutically acceptable: As used herein, the term "pharmaceutically acceptable," as applied to one or more, or all, component(s) of a composition as disclosed herein, means that each component must be compatible with the other components of the composition and not deleterious to a recipient thereof.

Pharmaceutically acceptable carrier: As used herein, the term "pharmaceutically acceptable carrier" refers to a pharmaceutically-acceptable material, composition, or vehicle, such as a liquid or solid filler, diluent, excipient, or solvent encapsulating material, that facilitates formulation of an agent (e.g., a pharmaceutical agent), modifies bioavailability of an agent, or facilitates transport of an agent from one organ or portion of a subject to another. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutical composition, formulation, or drug: As used herein, the term "pharmaceutical composition" or "formulation" or "drug" refers to a composition in which a therapeutic agent is formulated together with one or more pharmaceutically acceptable carriers.

Polypeptide: As used herein, "polypeptide" refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide can include one or both of natural amino acids and non-natural amino acids. In some embodiments, a polypeptide can include D-amino acids, L-amino acids, or both. In some embodiments, a polypeptide may include only L-amino acids. In some embodiments, a polypeptide may include one or more pendant groups or other modifications, e.g., one or more amino acid side chains, e.g., at the polypeptide's N-terminus, at the polypeptide's C-terminus, at non-terminal amino acids, or at any combination thereof. In some embodiments, such pendant groups or modifications may be selected from acetylation, amidation, lipidation, methylation, phosphorylation, glycosylation, glycation, sulfation, mannosylation, nitrosylation, acylation, palmitoylation, prenylation, pegylation, etc., including combinations thereof. In some embodiments, a polypeptide may be cyclic, and/or may include a cyclic portion. In some embodiments, a polypeptide can include at least 3, 4, 5, 6, 7, 8, 9, 10, 15, 20, 25, 30, 35, 40, 45, 50, 55, 60, 65, 70, 75, 80, 85, 90, 95, 100, 150, 200, 250, 300 or more residues.

Small molecule: As used herein, the term "small molecule" means a low molecular weight organic and/or inorganic compound. As used herein, the term "small molecule drug" is a drug whose active agent comprises a small molecule. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not and/or does not include a protein or polypeptide (e.g., is not an oligopeptide or peptide). In some embodiments, a small molecule is not and/or does not include a polynucleotide (e.g., is not an oligonucleotide). In some embodiments, a small molecule is not and/or does not include a polysaccharide; for example, in some embodiments, a small molecule is not a glycoprotein, proteoglycan, glycolipid, etc.). In some embodiments, a small molecule is not a lipid. In some embodiments, a small molecule is a modulating agent (e.g., is an inhibiting agent or an activating agent). In some embodiments, a small molecule is biologically active. In some embodiments, a small molecule is detectable (e.g., includes at least one detectable moiety). In some embodiments, a small molecule is a therapeutic agent. Those of ordinary skill in the art, reading the present disclosure, will appreciate that certain small molecule compounds described herein may be provided and/or utilized in any of a variety of forms such as, for example, crystal forms, salt forms, protected forms, pro-drug forms, ester forms, isomeric forms (e.g., optical and/or structural isomers), isotopic forms, etc. Those of skill in the art will appreciate that certain small molecule compounds have structures that can exist in one or more steroisomeric forms. In some embodiments, such a small molecule may be utilized in accordance with the present disclosure in the form of an individual enantiomer, diastereomer or geometric isomer, or may be in the form of a mixture of stereoisomers; in some embodiments, such a small molecule may be utilized in accordance with the present disclosure in a racemic mixture form. Those of skill in the art will appreciate that certain small molecule compounds have structures that can exist in one or more tautomeric forms. In some embodiments, such a small molecule may be utilized in accordance with the present disclosure in the form of an individual tautomer, or in a form that interconverts between tautomeric forms. In some embodiments, reference to a particular small molecule compound may relate to a specific form of that compound. In some embodiments, a particular small molecule compound may be provided and/or utilized in a salt form (e.g., in an acid-addition or base-addition salt form, depending on the compound); in some such embodiments, the salt form may be a pharmaceutically acceptable salt form. In some embodiments, where a small molecule compound is one that exists or is found in nature, that compound may be provided and/or utilized in accordance in the present disclosure in a form different from that in which it exists or is found in nature. Those of ordinary skill in the art will appreciate that, in some embodiments, a preparation of a particular small molecule compound that contains an absolute or relative amount of the compound, or of a particular form thereof, that is different from the absolute or relative (with respect to another component of the preparation including, for example, another form of the compound) amount of the compound or form that is present in a reference preparation of interest (e.g., in a primary sample from a source of interest such as a biological or environmental source) is distinct from the compound as it exists in the reference preparation or source.

Therapeutic agent or drug: As used herein, the term "therapeutic agent" or "drug" refers to any agent that elicits a desired pharmacological effect when administered to a subject. In some embodiments, an agent is considered to be a therapeutic agent if it demonstrates a statistically significant effect across an appropriate population. In some embodiments, the appropriate population can be a population of model organisms or a human population. In some embodiments, an appropriate population can be defined by various criteria, such as a certain age group, gender, genetic background, preexisting clinical conditions, etc. In some embodiments, a therapeutic agent is a substance that can be used for treatment of a disease, disorder, or condition. In some embodiments, a therapeutic agent is an agent that has been or is required to be approved by a government agency before it can be marketed for administration to humans. In some embodiments, a therapeutic agent is an agent for which a medical prescription is required for administration to humans.

Unit dose: As used herein, the term "unit dose" refers to an amount administered as a single dose and/or in a physically discrete unit of a pharmaceutical composition. In many embodiments, a unit dose contains a predetermined quantity of an therapeutic agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose can be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose can be present in a formulation that includes any of a variety of components in addition to the therapeutic agent(s). For example, acceptable carriers (e.g., pharmaceutically acceptable carriers), diluents, stabilizers, buffers, preservatives, etc., can be included. It will be appreciated by those skilled in the art that, in many embodiments, a total appropriate daily dosage of a particular therapeutic agent can include a portion, or a plurality, of unit doses, and can be decided, for example, by a medical practitioner within the scope of sound medical judgment. In some embodiments, the specific effective dose level for any particular subject or organism can depend upon a variety of factors including the disorder being treated and the severity of the disorder; activity of specific therapeutic agent employed; specific composition employed; age, body weight, general health, sex and diet of the subject; time of administration, and rate of excretion of the specific therapeutic agent employed; duration of the treatment; drugs and/or additional therapies used in combination or coincidental with specific compound(s) employed, and like factors well known in the medical arts.

Vessel: As used herein, in certain embodiments, the term "vessel" refers to a container that is sufficient to contain and/or enclose a single unit dose. In various embodiments, a vessel can be sufficient to contain and/or enclose multiple unit doses. In various embodiments, a vessel can be a vial (e.g., a cryovial or other vial), tube (e.g., a test tube or other tube), multi-well plate, ampule, bottle, bag, box, pouch, patch, syringe, blister pack, strip pack, sealed foil, cell culture bag, intravenous (IV) solution bag, cryobag, vitrification straw, drug delivery device, or other pharmaceutically acceptable vessel known in the art. In various embodiments a vessel can be composed of one or more of plastic, glass, laminated paper, metal, foil (e.g., a metal foil or plastic foil), or other pharmaceutically acceptable material for containing and/or enclosing a pharmaceutical agent. In various embodiments a vessel contains and/or encloses one or more unit doses of a pharmaceutical agent. In various embodiments a vessel is empty in that it does not contain and/or enclose, and/or has not been loaded with, a pharmaceutical agent.

Viral vector: As used herein, plasmid or viral vectors are agents that transport the disclosed nucleic acids (e.g., a therapeutic agent) into the cell without degradation and include a promoter yielding expression of the gene in the cells into which it is delivered. In some embodiments, the promoters are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also disclosed are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Viral vectors can have higher transfection (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

FIG. 1 is a block flow diagram showing an example process 100 for financing of a HCT drug administered to a HCT beneficiary, according to an illustrative embodiment. In this example, "Patient" is the HCT beneficiary, "Specialty Pharmacy" is the entity that receives and fills the prescription for the HCT, "Self-Insured Employer Group (SIEG) or their agent" is the borrower/payer, "Manufacturer" is the manufacturer of the HCT, and "octaviantFinancial (OFX)" is the lender. In other embodiments, the borrower/payer may not be a SIEG but rather is a state-backed (or other public) insurance plan, other third party health insurance provide, or other third party. Furthermore, in other embodiments, the tasks of the Specialty Pharmacy are handled by the manufacturer directly, or a distributor, wholesaler, hospital (e.g., a 340b pharmacy), or other third party. At "Start" 102 in the embodiment shown in FIG. 1, the Patient is prescribed a HCT drug 104, which, in certain embodiments, begins the "episode of care". In other embodiments, the episode of care begins at the execution of the term sheet or loan documents, or at another point in time decided upon by the lender and key stakeholders (e.g., the payer, manufacturer, etc.). The Specialty Pharmacy receives the prescription 106 and transmits a corresponding prescription claim to SIEG 108, who receives it and determines the eligibility of the prescription claim. In this example, SIEG either approves the prescription claim or denies it 110. If SIEG denies the claim, the process ends 112. If SIEG approves the claim, it determines if the manufacturer or other party offers a warranty 114. If so, SIEG may choose to purchase the warranty through the manufacturer 116 (e.g., a warranty that the drug will be efficacious for the patient). If not, SIEG decides whether or not to pay in full for the drug and/or for the warranty 118. If SIEG pays for the drug, the specialty pharmacy receives payment 120 and dispenses the drug to the patient 122, and the process ends 124. If SIEG does not pay in full, SIEG applies for financing of the drug and/or for the warranty 126. The lender/financing company evaluates SIEG for financing of the drug and/or the warranty 128. If financing is not approved 130, the SIEG pays the Specialty Pharmacy in full for the drug 132 and the patient receives the drug. If financing is approved for the SIEG, the financing process is completed through the lender's IT platform 134 (e.g., as described herein) for setting terms of one or more instruments (e.g., loan and/or warranty) in the HCT financing. Upon completion, OFX disburses funds 136 and the Specialty Pharmacy receives payment and dispenses the drug to the patient. Finally, any payments from SIEG (whether one time or regularly recurring, e.g., monthly or quarterly) may be managed by a third party for the term of the loan 138, whereupon the process 100 ends 140.

Figure 2:
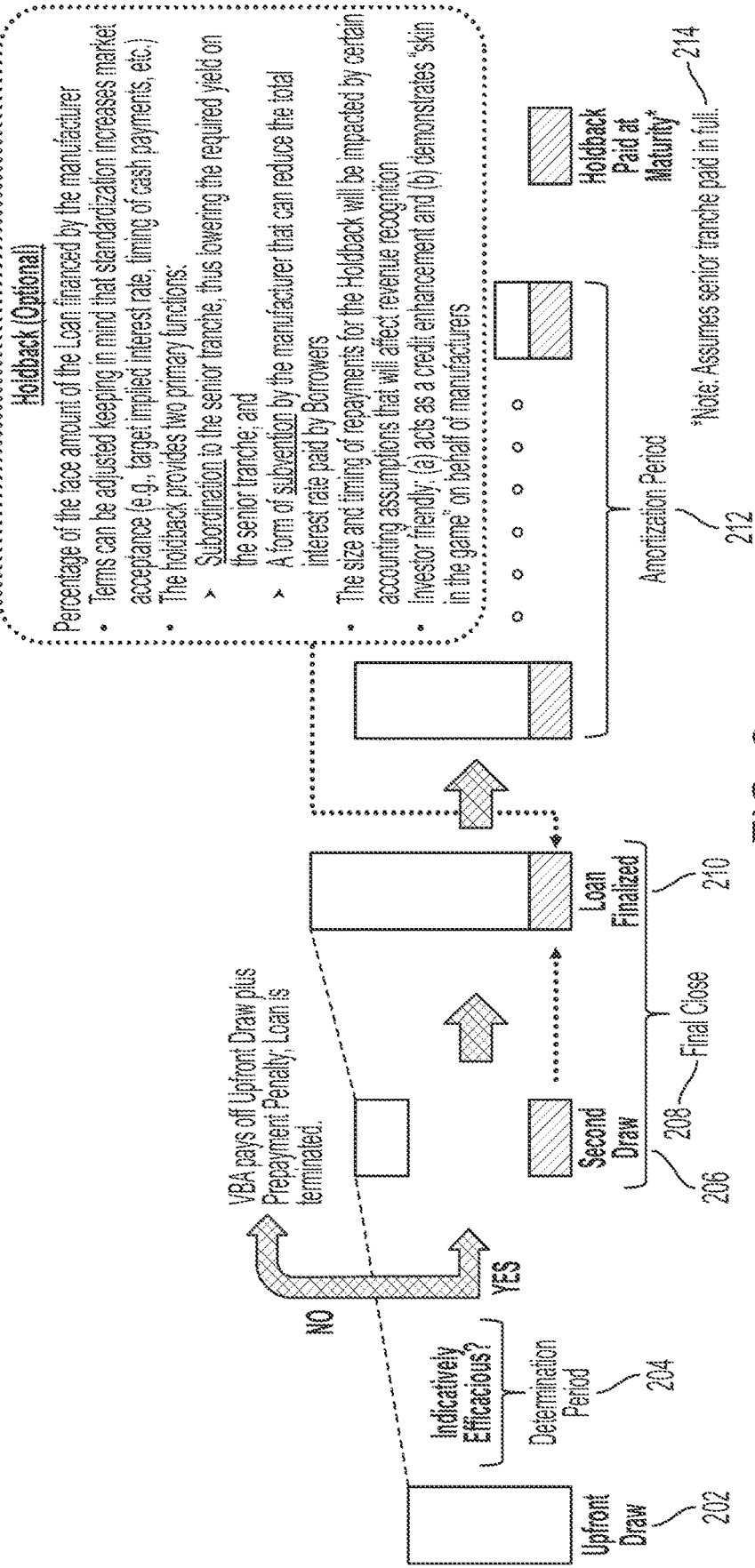
FIG. 2 is a flow diagram of the structure and terms of a loan in the financing of a HCT, according to an illustrative embodiment.

FIG. 2 is a flow diagram 200 of the structure and terms of an example loan in the financing of a HCT, according to an illustrative embodiment. The size of the loan may range, for example, from about 0.5 million to about 2.0 million USD, and has a tenor/maturity date, for example, 5 years. The use of proceeds is to fund (a) the price of the HCT, (b) a value-based agreement premium (VBA premium), (c) bundled expenses, defined as approved costs and expenses of pre- or post-therapy therapeutic treatments and services, (d) procedure-related costs, (e) the OBA fee, and (f) an arrangement fee. As referenced in FIG. 2, in this example, the borrower is the payer of the HCT (current and subsequent, if applicable), the HCT beneficiary is the individual who is the recipient of the HCT, and the guarantor is the employer of the policyholder of the policy that covers the HCT beneficiary.

In this example, the lender pays an Upfront Draw 202 (e.g., 77% of the HCT Price, e.g., a GCT, e.g., a one-dose or finite-dose drug, plus procedure-related costs, plus an initial outcomes benefit administrator (OBA) fee, plus the VBA premium, plus the arrangement fee) around the time of (e.g., immediately before, the day of, or shortly after) administration of the HCT to the HCT beneficiary. In certain embodiments, the Upfront Draw 202 is a percentage of the HCT price (e.g., cost of the drug charged by the manufacturer) plus certain procedure-related costs and/or the value based agreement premium cost, and/or initial outcomes benefit administrator (OBA) fee and/or pre-therapeutic bundled expenses and/or an arrangement fee. After a Determination Period 204 has elapsed (e.g., a period of time on the order of weeks up to several months, depending on the therapy), a determination is made regarding whether the drug is at least initially efficacious for the beneficiary. For example, for a GCT, a determination is made as to whether the therapy has successfully been transfected into the patient/beneficiary and/or whether it has generated an adverse response which would render the therapy ineffective or undesired. If the determination is that the therapy is not efficacious the warranty pays off the Upfront Draw 202 plus a Prepayment Penalty and the Loan is terminated. If the determination is that the therapy is at least initially efficacious for the beneficiary, the lender pays a Second Draw 206 (in this example, 13% of the cost of the HCT plus an estimate of the post-therapeutic bundled expenses, plus anticipated remaining OBA fees) and the Loan is Finalized 210 (e.g., at Final Close 208).

In this example, following an Amortization Period 212, there is a Holdback 214, which is a percentage of the face amount of the Loan financed by the manufacturer of the HCT. Terms of the Holdback 214 can be adjusted keeping in mind that standardization may increase market acceptance (e.g., target implied interest rate, timing of cash payments, etc.). In certain embodiments, the Holdback 214 is subordinated in right of payment pursuant to an agreement among the lenders (inclusive of the manufacturer). The Holdback provides two primary functions: subordination to the Senior Tranche (paid by the lender), thus lowering the required yield on the senior tranche, and a form of subvention by the manufacturer that can reduce the total interest rate paid by the borrower(s). The size and timing of repayments for the for the duration of the Episode of Care. The Episode of Care and Pre-Existing Condition facilitate portability for the Loan and/or Warranty. If this structure is incorporated into HCT payment schemes, it is estimated the Total Addressable Market for HCT will increase from $4.8 billion to over $30 billion.

TABLE 1

Certain Definitions

| Term | Definition |
|---|---|
| Site: | $[0.5-2.0] million |
| Tenor/Maturity Date: | [5] years |
| Coupon: | [[Term SOFR/Daily Simple SOFR] + [spread] + TBD% |
| Use of Proceeds: | To fund (a) HCT Price, (b) value-based agreement premium (VBA Premium), (c) Bundled Expenses, defined as approved costs and expenses of pre- or post-therapy therapeutic treatments and services, (d) Procedure-Related Costs, (e) the OBA fee, and (f) Arrangement Fee |
| Borrower: | Payer of the HCT (current and Subsequent, if applicable) |
| HCT Beneficiary: | The individual who is the recipient of the HCT |
| Guarantor: | Employer of the policyholder at time of treatment |
| Portability: | These specific terms facilitate portability for the Loan and the VBA Pending industry acceptance, they can be incorporated into all HCT payment schemes, thus increasing TAM (est.) from $4.8 billion to $30+ billion. |
| Upfront Draw: | (i) [77]% of the HCT Price, plus (ii) Procedure-Related Costs, plus (iii) Initial OBA Fee, plus (iv) the VBA Premium, plus (v) pre-therapeutic Bundled Expenses, plus (vi) the Arrangement Fee |
| Second Draw: | (i) [13]% of the HCT Price, plus (ii) an estimate of the post-therapeutic Bundled Expenses, plus (iii) anticipated remaining OBA Fees |
| Holdback: | [10]% of the HCT Price, deferred payment by Borrow to Manufacturer; subordinated in right of payment to the Facilities |
| Determination Period: | [TBD] period, during which time indicative efficacy is evaluated |
| Prepayment Penalty: | [TBD]% of total outstanding Loans |
| Episode of Care: | All services provided to the Beneficiary to treat the medical condition, including the HCT, Procedure-Related Costs and Bundled Expenses, beginning on the Prescription Date and ending on the Maturity Date |
| Pre-Existing Condition | The Beneficiary's underlying medical condition, which necessarily continues during the treatment with the HCT throughout the period during which Procedure-Related Costs and Bundled Expenses are incurred for the duration of the Episode of Care. |

Holdback 214 will be impacted by certain accounting assumptions that will affect revenue recognition and cash flows for the manufacturer. The Holdback 214 is investor friendly in that it (a) acts as a credit enhancement and (b) demonstrates risk taken on behalf of manufacturers. The Holdback 214 is paid at loan maturity, assuming the senior tranche is paid in full.

In the illustrative financing of FIG. 2, the Episode of Care is the period beginning on the Prescription Date and ending upon maturity of the Loan or Value-Based Agreement (VBA) (i.e., Warranty) during which all services are provided to the beneficiary to treat the medical condition, including the HCT, procedure-related costs, and bundled expenses. In other embodiments, the Episode of Care begins at the execution of the term sheet or loan documents, or at another point in time decided upon by the lender and key stakeholders (e.g., the payer, manufacturer, etc.). The Episode of Care covers the same time period as a contractually-defined Pre-Existing Condition, which is contractually defined as the underlying medical condition necessitating the HCT, which necessarily continues during the treatment with the HCT and throughout the period during which procedure-related costs and bundled expenses are incurred Table 1 above includes definitions of certain terminology that is used in FIG. 2, as well as elsewhere in the present disclosure.

Figure 2A:
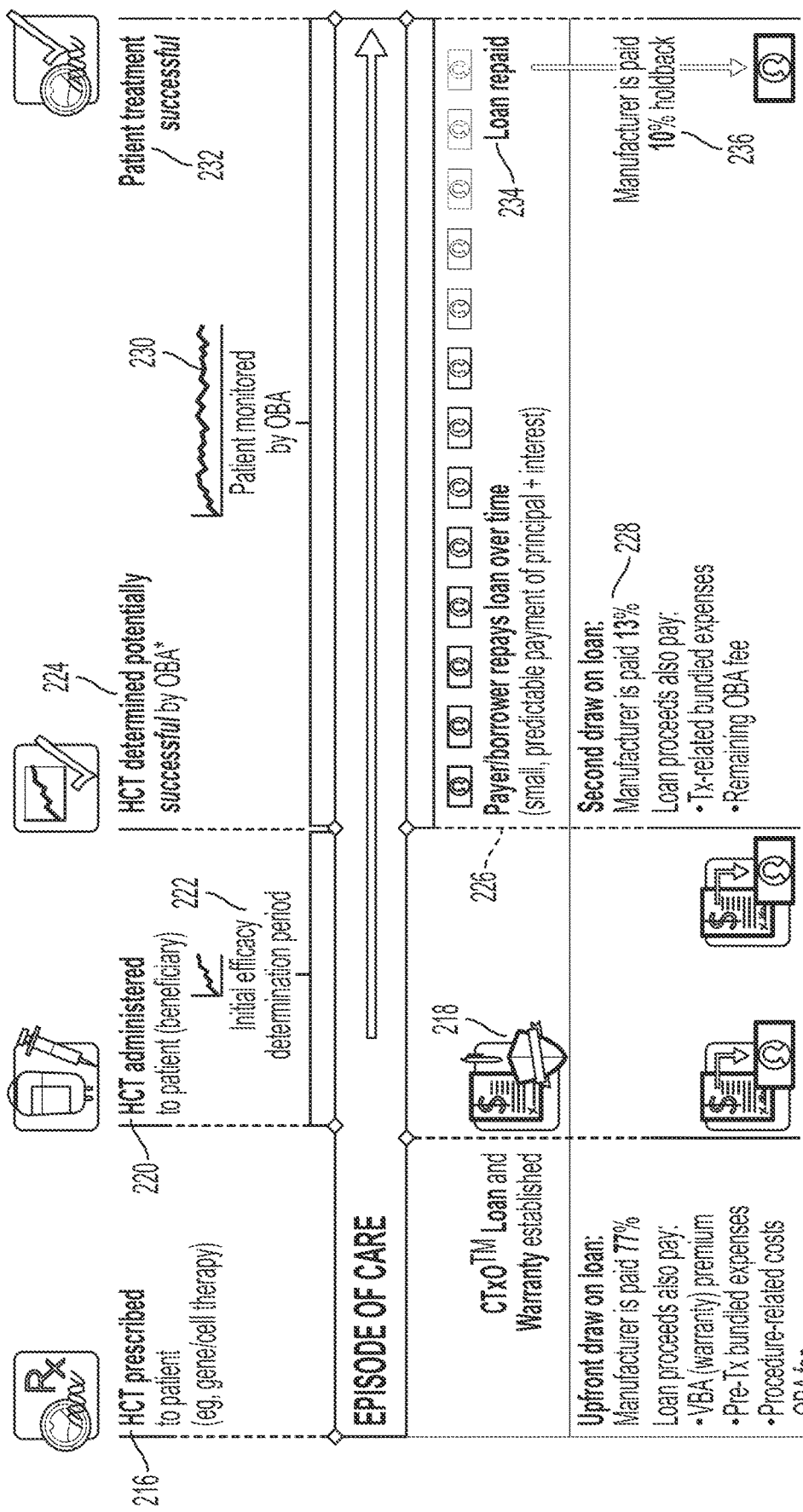
FIG. 2A is an illustrative example of a first scenario, according to aspects of the present embodiments.
Figure 2B:
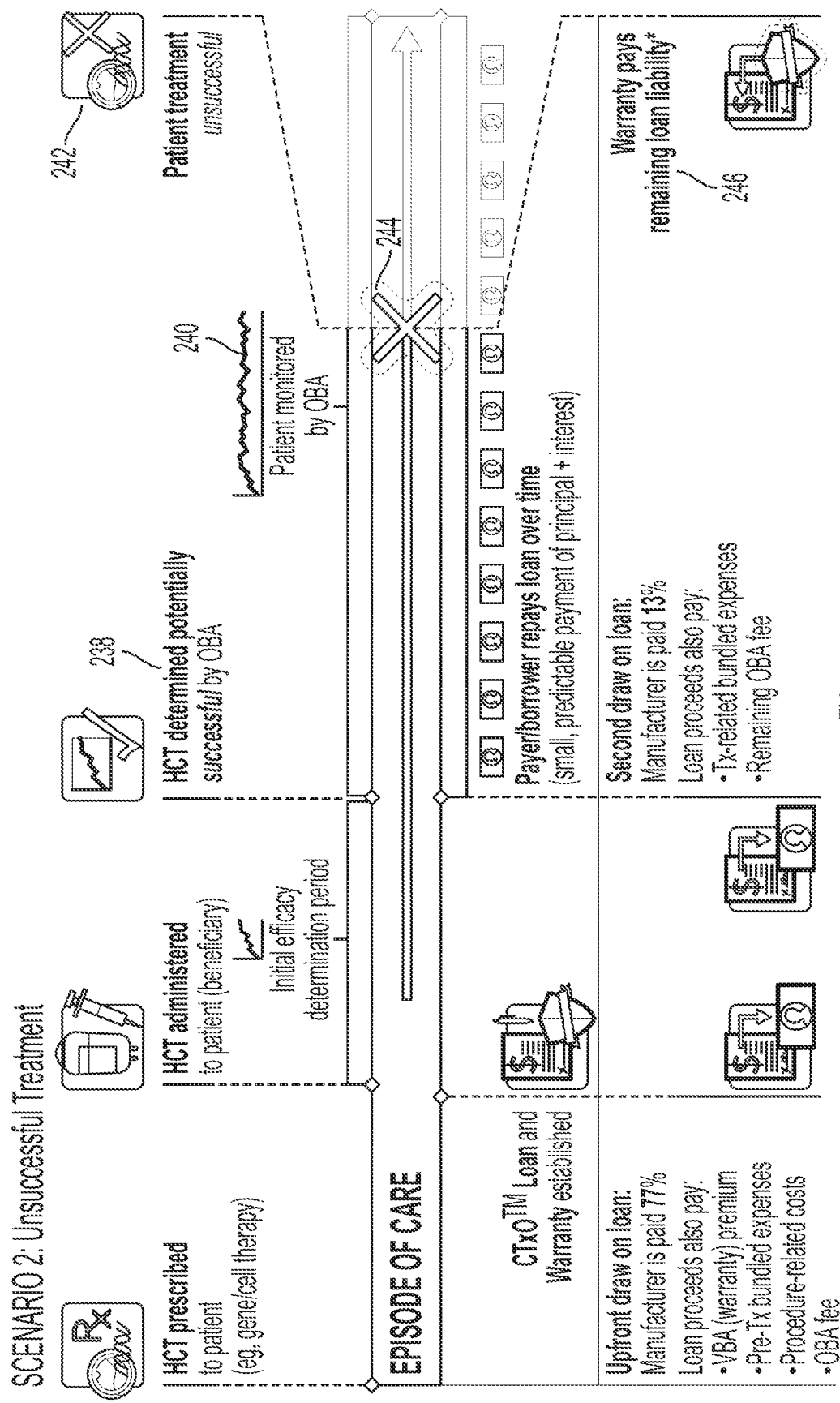
FIG. 2B is an illustrative example of a second scenario, according to aspects of the present embodiments.
Figure 2C:
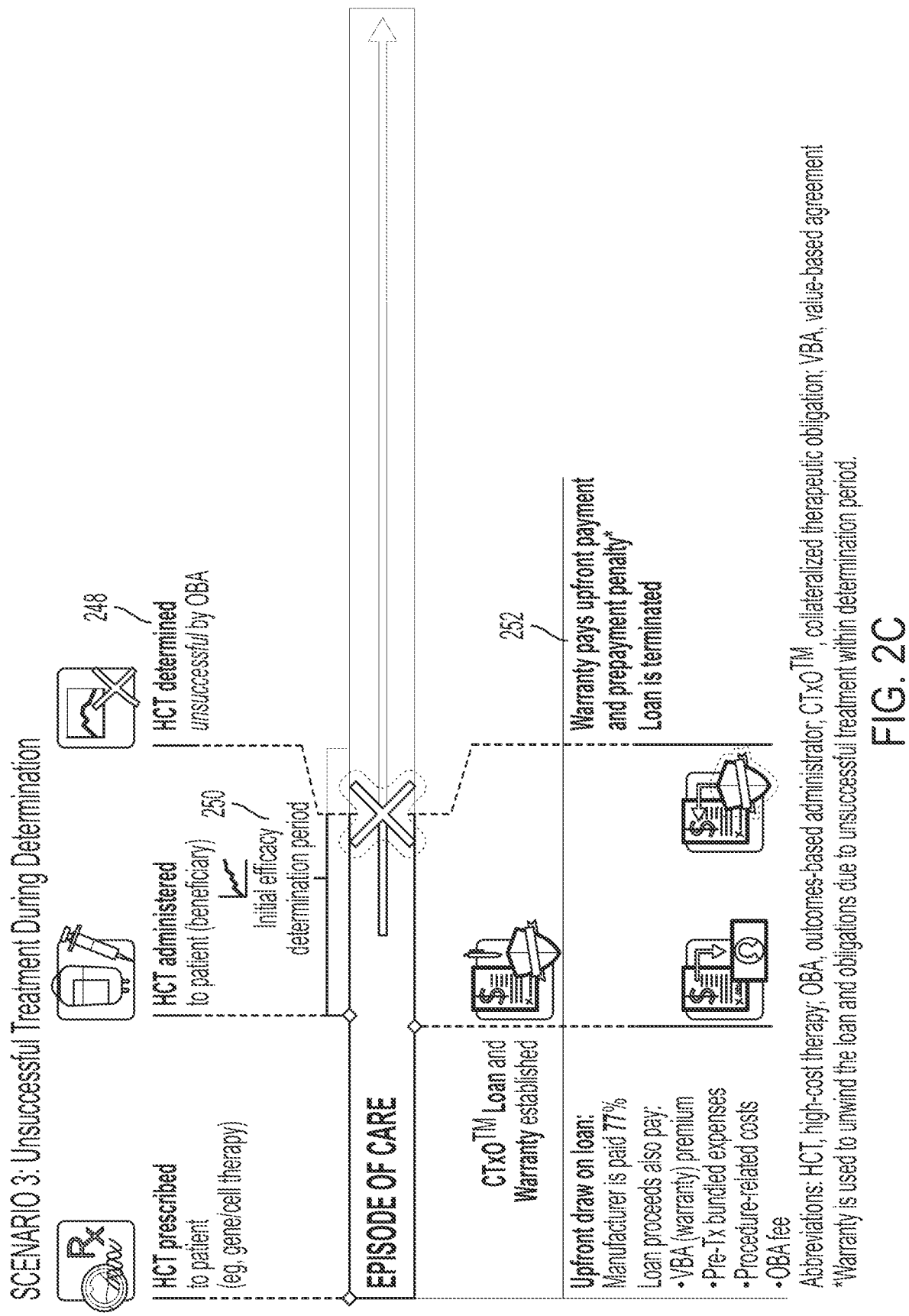
FIG. 2C is an illustrative example of a third scenario, according to aspects of the present embodiments.

FIGS. 2A, 2B, and 2C illustrate three possible scenarios, according to aspects of the present embodiments. In FIG. 2A, which illustrates a first scenario that includes a successful treatment, an HCT is prescribed 216 to a patient. Following the prescription 216 of an HCT to the patient, a collateralized therapeutic obligation (e.g., CTxO™) loan and warranty are established 218 whereby the manufacturer is paid 77% of the HCT price. The loan proceeds may also pay for VBA (warranty) premium, pre-treatment bundled expenses, procedure-related costs, the OBA fee, and/or other appropriate expenses. Very soon after the collateralized therapeutic obligation (e.g., CTxO™) loan and warranty are established 218 (i.e., almost immediately after), the HCT is administered 220 to the patient (or beneficiary). Once the HCT is administered, an initial efficacy determination period 222 is initiated. During the initial efficacy determination period 222, the patient is monitored to see if 1) the patient's body rejects the treatment, 2) the HCT doesn't take, 3) the HCT doesn't produce one or more expected proteins, and/or 4) the HCT proves to be otherwise ineffective. In scenario 1 illustrated in FIG. 2A, the HCT is determined to be potentially successful 224 by the OBA, at which time the initial efficacy determination period 222 concludes and the payer/borrower begins repaying 226 the loan. At the time the HCT is determined to be potentially successful 224 by the OBA, the manufacturer is paid 13% of the HCT price 228. Following the OBA determining the HCT is potentially successful 224, the patient continues to be monitored 230 by the OBA, and the payer/borrower continues to repay 226 the loan. In scenario 1, eventually, the patient treatment is determined to be successful 232 and the loan is repaid 234. At this time, the manufacture is paid 236 the remaining 10% of the HCT price.

FIG. 2B illustrates a second scenario in which the treatment is determined to be unsuccessful, according to aspects of the present embodiments. The second scenario is identical to the first scenario up until after the OBA determines the HCT to be potentially successful 238. In scenario 2, at some point during the monitoring 240 of the patient by the OBA, the OBA determines that the patient treatment is unsuccessful 242. At this time, patient monitoring is discontinued 244 and the remaining loan balance (or liability) is paid 246 by the warranty.

FIG. 2C illustrates a third scenario in which the treatment is determined 248 to be unsuccessful during the initial efficacy determination period 250, according to aspects of the present embodiments. In the third scenario, the OBA determines 248 that the treatment is unsuccessful during the initial efficacy determination period 250 (i.e., prior to the OBA determining the HCT to be potentially successful). In scenario 3, once the OBA determines 248 the treatment is unsuccessful, the warranty pays 252 upfront payment and prepayment penalties, and the loan is terminated.

Figure 3:
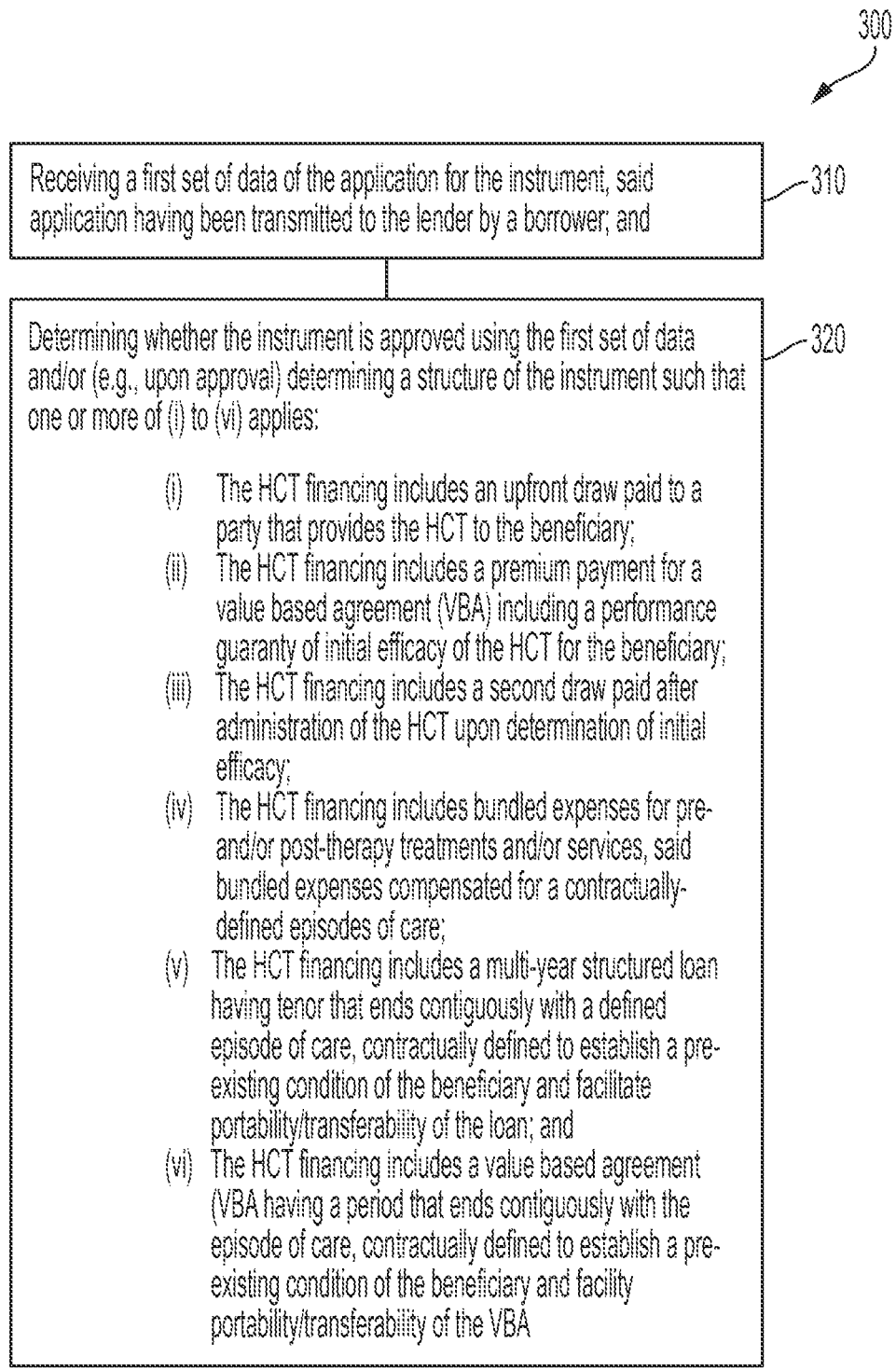
FIG. 3 is a block flow diagram of a method for financing a HCT, according to an illustrative embodiment.

FIG. 3 is a block flow diagram (300) of a method performed in the financing of a HCT, according to an illustrative embodiment. More specifically, the block flow diagram (300) illustrates a method for assessment, by a lender (e.g., a senior lender), of an application for an instrument (e.g., a multi-year structured loan and/or a warranty), and upon approval, for determination of one or more terms of the instrument, for financing one or more of (i), (ii), and (iii) as follows (collectively, the HCT financing): (i) a high cost therapy (HCT) [e.g., a gene or cell therapy (GCT), e.g., said HCT comprising a high-cost treatment, e.g., a GCT drug, e.g., a single or finite dose gene therapy, e.g., a single or finite dose cellular therapy, e.g., wherein the high cost therapy has a cost of at least 100,000 USD, e.g., at least 200,000 USD, e.g., at least 300,000 USD] to be administered to a HCT beneficiary (e.g., a person covered under a health insurance policy, e.g., a health insurance policy of an employer-sponsored health plan, e.g., a health insurance policy provided by a self-insured employer group (SIEG) or its agent) [e.g., wherein the financing of the HCT comprises one or more of an upfront draw (e.g., a first senior unsecured term loan), a second draw (e.g., a second senior unsecured term loan), and a holdback amount (e.g., an amount made available to a borrower by a manufacturer of the HCT)], (ii) bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary [e.g., wherein the financing of the bundled expenses comprises a delayed draw], and (iii) an associated performance-based guaranty of the (e.g., at least initial) efficacy of the HCT administered to the HCT beneficiary [e.g., said guaranty in the form of a warranty or other value based agreement (VBA)], wherein the instrument is structured in a manner to facilitate portability (e.g., transferability) of said instrument (e.g., transfer of liability from the borrower to a subsequent payer) over the tenor of the instrument.

In step 310, the method includes receiving (e.g., by a processor of a computing platform of the lender) a first set of data of the application for the instrument, said application having been transmitted to the lender by a borrower (e.g., the SIEG or its agent).

In step 320, the method includes determining (e.g., by the processor) whether the instrument is approved using the first set of data and/or (e.g., upon approval) determining [e.g., by the processor e.g., said processor utilizing stochastic and/or algorithmic and/or machine learning (and/or other forms of artificial intelligence (AI)) methodologies] a structure (e.g., one or more terms) of the instrument such that one or more of (i) to (vi) applies, as follows: (i) the HCT financing comprises an upfront draw paid to a party [e.g., a specialty pharmacy; e.g., a treatment facility (hospital, outpatient clinic); e.g., a pharmaceutical manufacturer] that provides and/or administers the HCT to the HCT beneficiary [e.g., wherein said upfront draw is at least 30% (e.g., at least 40%, at least 50%, at least 60%, at least 70%, or about 77%) of the cost of the HCT (e.g., plus procedure-related costs and/or VBA premium cost and/or initial outcomes benefit administrator (OBA) fee and/or pre-therapeutic bundled expenses and/or an arrangement fee)] and is made at or near the time of administration of the HCT to the HCT beneficiary (e.g., just prior to or after the therapy); (ii) the HCT financing comprises a premium payment for a value based agreement (e.g., a performance agreement, a warranty, or other insurance product) structured as a performance guaranty of initial efficacy of the HCT for the HCT beneficiary [e.g., wherein said initial efficacy is determined using predefined, measurable, reproducible and/or verifiable criteria (e.g., serum biomarkers, functional tests, etc.), e.g., wherein said criteria are agreed to by both the manufacturer of the HCT (e.g., the manufacturer of the GCT drug) and the lender or an outcomes benefit administrator (OBA) in advance of administration of the therapy (e.g., the GCT drug) to the HCT beneficiary]; (iii) the HCT financing comprises a second draw paid within an agreed-upon period of time after administration of the HCT and upon determination (e.g., by an identified OBA) of initial efficacy of the HCT for the HCT beneficiary [e.g., wherein said second draw covers the remainder of the cost of the HCT (e.g., plus an estimate of post-therapeutic bundled expenses and/or anticipated remaining outcomes benefit administrator (OBA) fees), or covers said remainder minus a manufacturer's holdback amount (e.g., 5-25%, e.g., 10%, of the cost of the HCT)]; (iv) the HCT financing comprises bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary, said bundled expenses being compensated for a contractually-defined episode of care, wherein said episode of care is a time period associated with the HCT for which a bundled payment (e.g., condition-specific capitation) is made (e.g., wherein said episode of care is contractually defined as a time period beginning when the HCT is prescribed to the HCT beneficiary and lasting until maturity of the instrument, e.g., the loan and/or the guaranty); (v) the HCT financing comprises a multi-year structured loan having a tenor that ends contiguously with a defined episode of care, wherein said episode of care is contractually defined to establish a preexisting condition of the HCT beneficiary, thereby facilitating portability and/or transferability of associated liability from the borrower (e.g., the SIEG or its agent) to another party [e.g., in the event of (and upon) exit of the policyholder from the borrower's health plan (e.g., and upon subsequent entry of the (now former) policyholder under a new health plan covering the HCT beneficiary)] while the HCT beneficiary is considered to have the pre-existing condition; and (vi) the HCT financing comprises a value based agreement (e.g., a performance agreement, a warranty, or other insurance product) having a period (e.g., warranty period) that ends contiguously with an episode of care, wherein said episode of care is contractually defined to establish a pre-existing condition of the HCT beneficiary, thereby facilitating portability and/or transferability of associated liability [e.g., in the event of (and upon) exit of the policyholder from the borrower's health plan (e.g., and upon subsequent entry of the (now former) policyholder under a new health plan covering the HCT beneficiary)] during the time the HCT beneficiary is considered to have the pre-existing condition.

Figure 4:
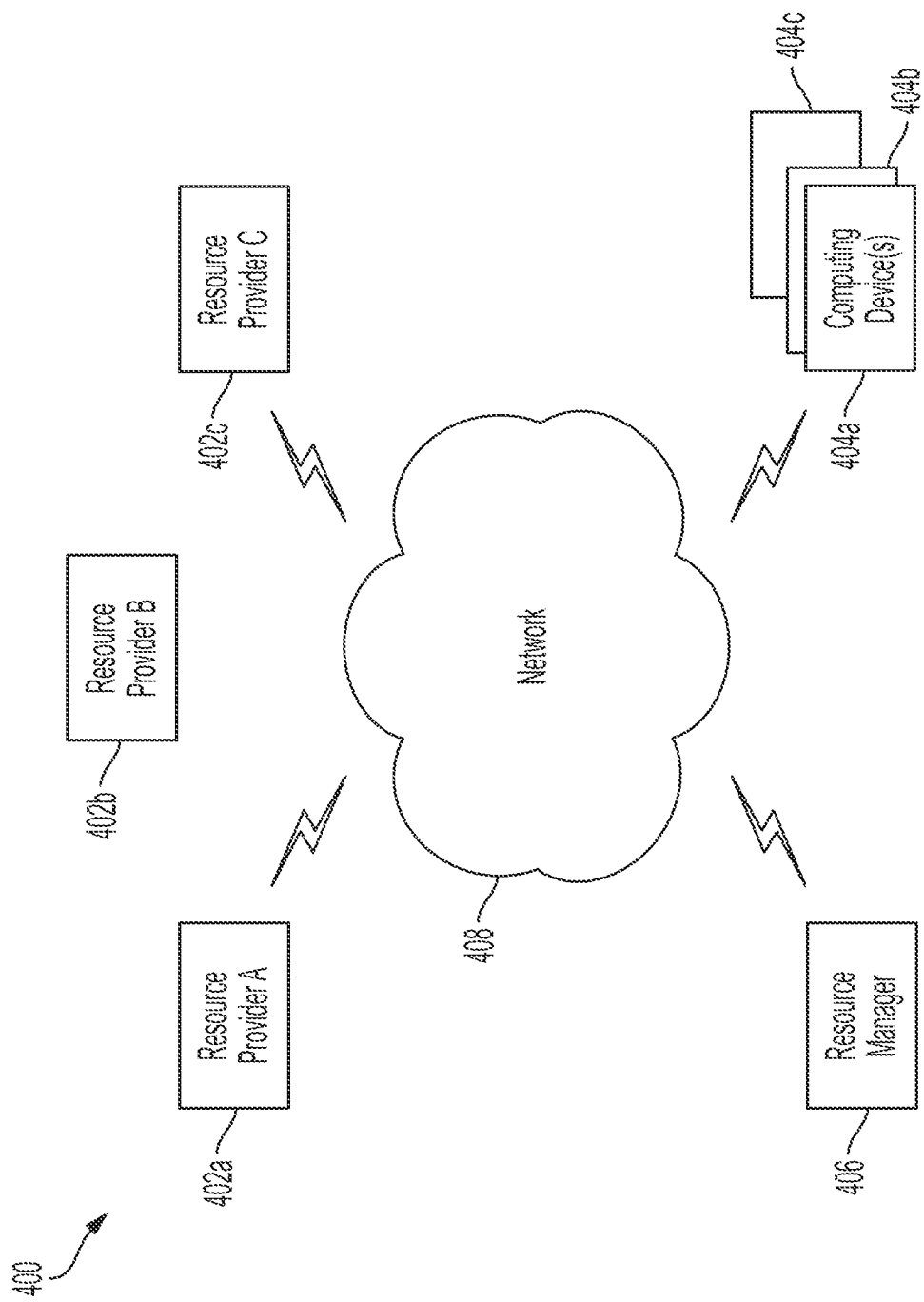
FIG. 4 is a block diagram of an exemplary cloud computing environment, used in certain embodiments.

FIG. 4 is a block diagram of an exemplary cloud computing environment, used in certain embodiments.

Figure 5:
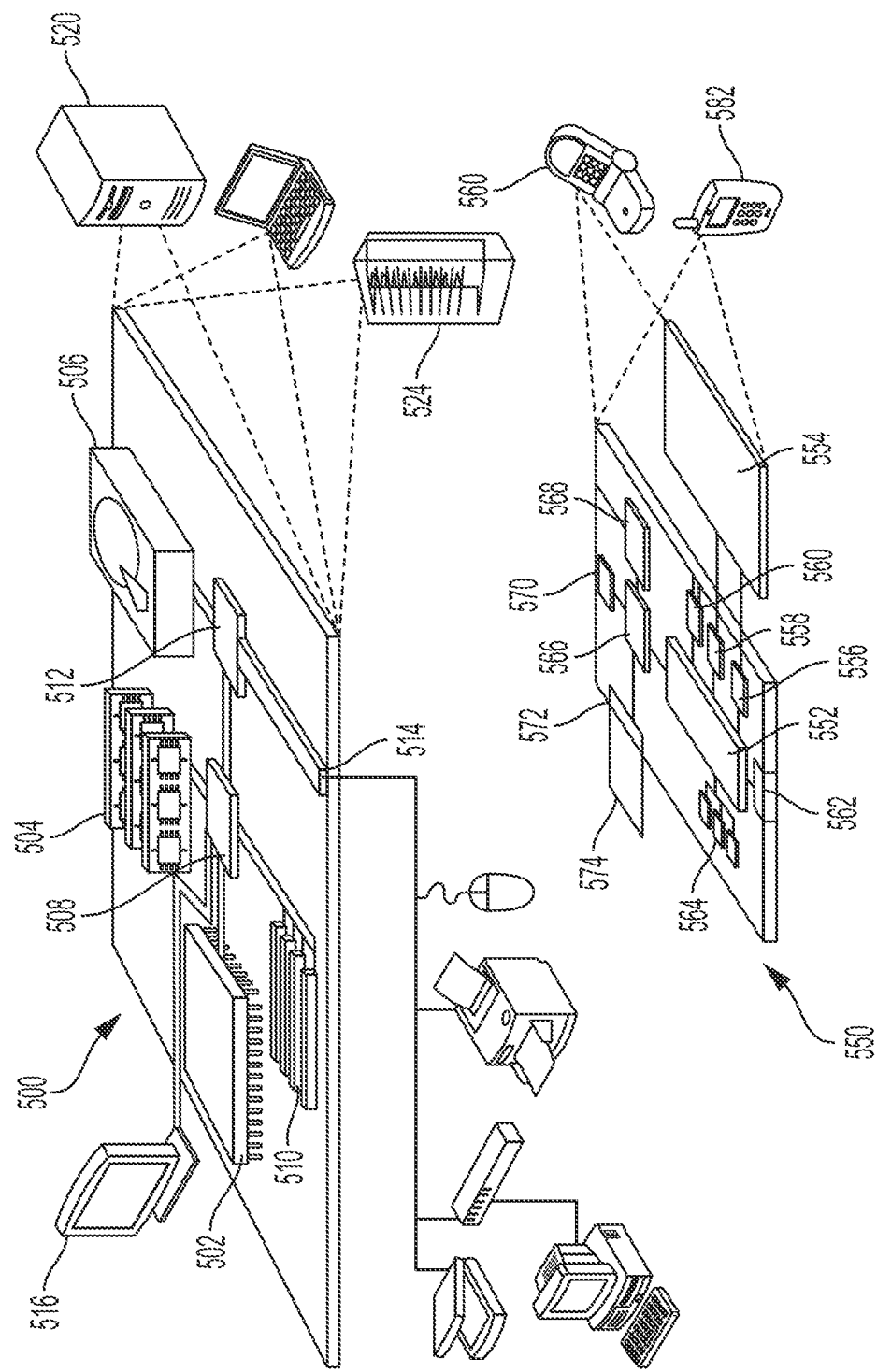
FIG. 5 is a block diagram of an example computing device and an example mobile computing device used in certain embodiments.

FIG. 5 is a block diagram of an example computing device and an example mobile computing device used in certain embodiments.

In certain embodiments, algorithms are used to automate the evaluation of risk in issuing a loan to a borrower by estimating an aggregate risk value from a set of facts and data about the borrower, where such evaluation of risk is used as a threshold condition to determine whether a borrower is approved for the loan terms using computer-executable instructions for causing the computer processor to be configured to: (i) retrieve the total cost of therapy from a third party who may aggregate average costs across a diverse network of care providers; and (ii) retrieve borrower credit data, including but not limited to one or more of the following: the borrower credit rating; prior history of default; current debt service; current capital structure; history of healthcare expenditures for beneficiary [e.g., whether the borrower is currently paying and/or previously paid a high cost therapy standard of care (HCT SOC)]; expenditures of the health plan in general; assets including one or more of accounts receivables, cash, inventories, prepaid expenses, securities, among others; real estate owned; other assets available to serve as collateral; liabilities such as account payables, notes payables, accrued expenses, short term debt, among others; cash flow including the last five years of operating cash flow, cash flow from financing, cash flow from investing, levered and unlevered free cash flow; financial auditing policies and auditors used to present the borrower's corporate finances; number of current employees; wage obligations; and other metrics deemed necessary to establish the borrower's credit risk, wherein one or more factors of the borrower credit data is used by one or more computer algorithms (e.g., artificial intelligence models) (computer-executable instructions) to determine the borrower aggregated risk value as compared to a threshold condition, where the algorithm outputs to an entity one more data points regarding the aggregate risk value as compared to a threshold condition.

In certain embodiments, algorithms are used to automate the loan terms using computer-executable instructions for causing the computer process to be configured to retrieve "Loan Factors", which may include one or more of the following: (i) the total cost of care, which may include one or more of the costs charged by a formulating pharmacy, the cost charged by the therapeutic manufacturer, a value-based agreement premium, e.g., which may be a pre-set number retrieved by the executable instructions or may be a number calculated by the algorithm; (ii) the determination period; (iii) the timing of cost of care over the determination period; (iv) the amount and/or percent of the upfront draw; (v) one or more data regarding the borrower and/or its credit data; (vi) data regarding the manufacturer preferred loan terms, which may include one or more of the following: amount and/or timing of cash payments, size and/or timing of holdback terms, or the like; (vii) the stated and/or probabilistically calculated efficacy of the GCT; (viii) data on the associated warranty, e.g., including its nature, cost, and/or terms; (ix) prevailing variable interest rate floors established by benchmarks such as LIBOR; (x) current market interest rates for loans of similar tenor and risk profile; (xi) market-wide default rates; (xii) pre-determined penalties for pre-payment; and (xiii) aggregate and/or individual risks, wherein the algorithm calculates the Loan Terms and Loan Structure, and auto-fills an offer term sheet and loan agreement.

In accordance with various aspects of the present disclosure, one or more of the Loan Factors (upfront draw percent, market interest rate, pre-payment penalties, etc.) and/or Loan Structure may be predefined and/or may be dynamically adapted by one or more computer systems locally and/or in a cloud-based system (e.g., any of the computer systems and/or networks described herein). This flexibility enables the prioritization of some Loan Terms and/or Loan Structures over others.

Deidentified clinical data may be supplied by the outcomes-based administrator for the purposes of internal analysis. These data may be used to statistically assess the continued durability of the GCT in the current beneficiary or for future efficacy and durability assessments of future beneficiaries receiving the same GCT. The data may also be used to assess patient compliance with the follow-up protocol as stipulated in the warranty and as agreed to by the manufacturer and the payer. In accordance with various aspects of the present disclosure, the efficacy of the GCT is saved for each loan and the patient profile, which may be one or more characteristics of the employee received by the lender, such as physical characteristics, age, genome sequence (full or partial), known medical history including date of diagnosis, among others. The GCT efficacy and patient profile data may therefore be analyzed and taken into consideration for future loans involving the specific GCTs.

In accordance with various aspects of the present disclosure, each loan may be pooled together to create new securities that may be marketed and sold to investors. In approaching investors, the lender may use data such as types and coverage of warranties, market feedback, appetite for risk to determine whether the new securities would be successful if the lender approaches a bank to securitize a loan.

Once GCT tracking is measured, adding additional GCT therapies to the loan pool will introduce new risk given that the efficacy and durability of the new GCT in the current beneficiary has yet to be determined, or may have high error associated with efficacy given a small sample pool of patients that have undergone the new GCT. Various algorithms may be used to balance the portfolio, including analyzing fees paid to the lender based on the characteristics of the loan pool and the nature of the GCT therapies that comprise it.

In accordance with various aspects of the present disclosure, the algorithms discussed herein may apply one or more heuristics to enable a rapid decision process based on priorities and policies set by one or more entities involved in the contemplated invention. This may be particularly important in situations where the amount of time permitted to reach a decision is short. In certain embodiments, decision making may be done automatically by the AI within preset constraint limits.

In accordance with aspects of the present disclosure, the algorithm may request assistance from one or more entities for guidance, when the algorithm has incomplete information input and is unable to arrive to a conclusion.

Algorithms

Embodiments described herein may include the use of one or more algorithms to enhance and/or optimize the features of various embodiments. Algorithms may include, but are not limited to, for example, artificial neural networks, multi-objective optimization, stochastic variables, probability and statistics, stochastic calculus, decision trees, random forests, linear and/or non-linear programming, regression, artificial intelligence, machine learning, Monte Carlo, or other techniques used for optimization and/or predictive analysis. It is understood by one skilled in the art that when these techniques are specifically mentioned in the description of the algorithms below, this does not exclude application of other techniques in the same algorithm.

Optimize Holdback Level and/or Timing

The holdback amount and timing may be determined by one or more algorithms. These may be independently optimized or may be simultaneously optimized via multi-objective optimization. Inputs into the algorithm may include one or more of the following pieces of data regarding financial information from the company, such as pharmaceutical total revenue, pharmaceutical revenue from target GCT sales, pharmaceutical revenue projections, projected therapeutic approvals over 5 years that may impact revenue, pharmaceutical goal revenue recognition per unit time (monthly, quarterly, yearly), and any other financial information from the company.

Optimize Interest Rate

The loan interest rate is the principal means for revenue generation. It may be independently optimized or may be simultaneously optimized via multi-objective optimization. Given a set of GCTs and estimates for each GCT efficacy, in conjunction with other market and/or cost data, a Pareto frontier is generated identifying the optimal loan interest rate.

Forecast Future Revenue

Future portfolio revenue may be estimated by analyzing data including historic and/or estimated GCT efficacy, GCT demand, GCT supply, and/or other input data. Stochastic analysis of outcomes under various scenarios may be used to predict future revenues. Similar techniques such as stochastic calculus may be employed to predict the time evolution of revenues under a variety of initial conditions.

Forecast Portfolio Balance

Stochastic analysis, stochastic calculus, and/or Monte Carlo techniques may be used to forecast the balance of various GCT used. Forecasting GCT balance may be used to identify demand trends and may also be used to adjust loan interest rate and/or termination fee to optimally situate the GCT portfolio with respect to market conditions.

Incorporation of New GCTs

Addition of a new GCT to an existing portfolio introduces risk as the efficacy of the new GCT may not be known with high precision. The potential variability of the GCT efficacy may lead to higher variance in forecasted revenues. Multi-objective optimization, artificial neural networks, artificial intelligence, and/or Monte Carlo techniques may be employed to quantify portfolio risk prior to adoption of a new GCT.

Adjust Interest Rate and/or Termination Fee for Individual GCTs

Portfolio optimization or prevailing market conditions may require the interest rate to be different for different GCTs. GCTs will likely have different efficacies, demands, supplies, and costs. This may lead to optimization outcomes with different interest rates associated with different GCTs. Multi-objective optimization, stochastic analysis, and/or Monte Carlo techniques may be employed to optimize these parameters across a portfolio of GCTs.

Forecast Future Demand

Stochastic analysis and/or stochastic calculus may be used to forecast future demand for one or more GCTs. Historic demand, supply, estimates of the treatable population, market expansion, and/or future cost estimates may be leveraged by these techniques to estimate the future demand of GCTs under a variety of scenarios and initial conditions.

Forecast Future Supply

Stochastic analysis and/or stochastic calculus may be used to forecast future supply for one or more GCTs. Historic demand, supply, estimates of the treatable population, market expansion, and/or future cost estimates may be leveraged by these techniques to estimate the future supply of GCTs under a variety of scenarios and initial conditions.

Forecast Future Treatable Population

Stochastic analysis and/or stochastic calculus may be used to forecast future treatable population for one or more GCTs. Historic demand, estimates of the treatable population, market expansion, and/or future cost estimates may be leveraged by these techniques to estimate the future treatable population of GCTs under a variety of scenarios and initial conditions.

Forecast Future Costs

Stochastic analysis and/or stochastic calculus may be used to forecast future costs for one or more GCTs. Historic demand, estimates of the treatable population, market expansion, and/or future cost estimates may be leveraged by these techniques to estimate the future costs of GCTs under a variety of scenarios and initial conditions.

Securitization Optimization

Determining which loans to bundle together for securitization may be accomplished using multi-objective optimization, Pareto analysis, and/or stochastic analysis. Market conditions are examined to determine the optimization factors and/or prioritization of such factors used in the analysis. The result is a set of bundles suggested for securitization. These bundles may not be disjoint, allowing for selection preference by portfolio managers.

Algorithms, Generally

In accordance with various aspects of the present disclosure, the algorithms discussed herein may, for example, apply more complex reasoning solutions in the area of multi-objective optimization techniques to make decisions regarding selection of borrower aggregated risk value, Loan Terms, and/or Loan Structure. Such multi-objective optimization techniques may take in consideration different optimization goals of the entities involved. These techniques, and the success of the decisions, may be based on information about the past decisions of the algorithm in certain scenarios, and outcomes.

In accordance with various embodiments described herein, the algorithms may include one or more of the following methods of analysis and optimization: case-based reasoning with displacement analysis, mechanical linkage analysis, optimized stiffness-displacement analysis, Procrustes-based pairwise optimization, blackboard framework, case-based reasoning, CDR augmented two dimensional geometric overlay, directed graph theory using tolerance analysis, displacement optimization, displacement optimization using genetic algorithms, displacement optimization using penalty-function methods, finite element analysis, finite element and nonlinear rigid body dynamics analysis, force analysis using particle swarm optimization, force and moment analysis, force and moment equilibrium analysis, genetic-algorithm based optimization using screw theory, genetic algorithms, genetic algorithm optimization, genetic algorithm optimization using finite element analysis, genetic algorithm-based optimized stiffness-displacement analysis, geometric and kinetic model analysis, geometric constraint based reasoning, geometric reasoning, geometry and graphical force analysis, geometry and rule-based approach, geometry-based reasoning, graph approach, graph theory using tolerance analysis, graph theory using tolerance factors, graph theory using tolerance normalization, group technology/neural network, heuristic preferences with screw-set theory, heuristic rule-base, heuristic rule-based approach with geometric reasoning, kinematic algorithm, kinematic variation analysis, multi-criteria optimization, multi-objective optimization using an interchange algorithm, neural network, non-optimized evolutionary algorithm, nonlinear optimization algorithm, object oriented reasoning with fuzzy set optimization, parametric modeling, precedence matrix with genetic algorithm, pseudo-gradient based optimization, qualitative rule-based analysis, rule induction and re-use, rule-based approach, rule-based approach augmented with various features, rule-based approach featuring graph analysis, stability analysis, tolerance sensitivity analysis, rule-based with displacement analysis, stiffness-displacement analysis, stress fracture analysis, swept volume analysis, tolerance analysis, or any other suitable technology.

Constructive Example—Financing of Zolgensma® (Onasemnogene Abeparvovec-Xioi) Administered to a HCT Beneficiary The following is a hypothetical, illustrative scenario in which a payer utilizes the HCT financing instrument (referenced in this example as the "HCT instrument") for a beneficiary requiring Zolgensma therapy delivered through the channel of a specialty pharmacy is offered. Zolgensma is one of two high-cost gene therapies currently commercialized in the United States and, as such, was chosen as a practical example to illustrate the application of the instrument and the processes and procedures by which it can be utilized in conjunction with high-cost gene therapies that may be approved by the FDA. In portions of this example it may be assumed, solely for the purposes of this illustration, that an association between the Applicant and the manufacturer of Zolgensma (AveXis/Novartis) exists, though no such relationship is currently in effect or likely to be in effect. AveXis/Novartis is not affiliated with the Applicant and has not endorsed, approved or otherwise opined on the HCT instrument either in part or in whole. Use of Zolgensma in this illustrative example should not be construed or interpreted to mean that the Applicant has made any representation concerning the utilization of the HCT instrument in conjunction with Zolgensma now or at any time in the future or that a relationship between the Applicant and the manufacturer (AveXis/Novartis) currently exists or may exist. Further, utilization of the HCT instrument by the payer, whether in part or whole, is not dependent on the pre-existence of any relationship between the Applicant and any pharmaceutical manufacturer.

Zolgensma, Onasemnogene abeparvovec, is a gene therapy developed by AveXis/Novartis and approved by the FDA in 2019 for use in children under the age of two as a treatment option for spinal muscular atrophy, a neuromuscular disorder arising from mutations in the SMN1 gene that results in the loss of motor neurons, progressive muscle wasting and, frequently, death. Using the viral vector AAV9, Zolgensma works by delivering to the recipient's affected motor neurons via intravenous infusion a functional SMN1 transgene under the regulatory control of synthetic promoters. The therapy carries a list price of approximately $2.1 MM.

Once a determination is made by a healthcare provider (HCP) that Zolgensma therapy would be of benefit to a covered beneficiary, a process begins whereby the payer is notified for purposes of granting prior authorization. If the payer chooses to utilize the HCT instrument, the payer would contact the Applicant—acting as the financing company—to apply for a HCT instrument utilizing a set of formalized submission procedures and guidelines established by the Applicant. Upon receipt of the payer's HCT instrument application, the Applicant would determine the terms of financing arrangement based on the criteria previously outlined in this claim and in conjunction with any holdback percentage that AveXis/Novartis may utilize as a form of subvention to financing along with the availability of a value based agreement.

In this hypothetical example, a warranty may be available to the payer for a premium in which the efficacy of Zolgensma may be guaranteed in proportion to the remaining loan payments. The period of warranty effectiveness along with the tenor of the loan financing would establish the episode of care. In other embodiments, the episode of care begins at the execution of the term sheet or loan documents, or at another point in time decided upon by the lender and key stakeholders (e.g., the payer, manufacturer, etc.). With respect to Zolgensma, efficacy may be defined as preventing death or the need for permanent ventilatory support consisting of >16 hours of respiratory assistance per day continuously for >14 days or some other metric consistent with outcome criteria established during the Zolgensma clinical or post-marketing evaluation periods. Other metrics such as scoring on the Children's Hospital of Philadelphia Infant Test of Neuromuscular Disorders (CHOP-INTEND) may be utilized at the discretion of the underwriting party at their sole discretion. The warranty may be provided by AveXis/Novartis, an AveXis/Novartis affiliate, the Applicant, an affiliate of the Applicant or a separate third-party underwriter.

For this hypothetical, it is assumed that the loan principal consists of the $2.1 MM cost of Zolgensma and a $200,000 premium for the warranty, and $50,000 infusion costs ($2.305 MM total), to be repaid over a four-year episode of care with 8% fixed interest, compounded monthly over the instrument's tenor ($2,753,777.64 total principal and interest payments, paid in $57,370.37 monthly installments) with a 10% holdback.

If the payer agrees to these terms, the payer would grant authorization for Zolgensma to the HCP who would then receive the therapy via "white-bag" from AveXis/Novartis, or an associated specialty pharmacy (e.g. Orsini, Accredo) dispensing Zolgensma, upon "closing" of the loan. At closing, the dispensing entity would receive from the Applicant (acting as the source of financing) 77% ($1.617 MM) of the $2.1 MM Zolgensma cost. The HCP would then administer the therapy to the beneficiary. After a two-week determination period in which the beneficiary was monitored by an independent, third-party outcomes based administer (OBA), the dispensing entity would receive an additional 13% ($273,000) if certain criteria were met (e.g. whether the beneficiary was still alive and not requiring extensive ventilator support). At this time, the loan would be finalized and the payer would begin making periodic principal (inclusive of the cost of Zolgensma plus the warranty product premium, initial outcomes benefit administrator (OBA) fees, and procedure-related costs) and interest payments to the Applicant. If the determination criteria were not met (e.g. the beneficiary did not survive) the loan would unwind and the warranty would pay the remaining loan liability and prepayment penalty.

Over the course of the next four years, i.e., in this example, the contractually defined "episode of care", the payer would make continued monthly principal and interest payments of $57,370.37 to the Applicant and the beneficiary would be monitored by the OBA to assess whether the conditions of the warranty have been satisfied. If, after four years, the provisions of the warranty were not triggered and the payer satisfied their loan obligation, AveXis/Novartis, or the associated dispensing specialty pharmacy, would receive a bullet payment in the amount of $210,000 or 10% of the cost of Zolgensma, and the episode of care would conclude.

Furthermore, the aforementioned loan may be part of a bundle of loans for purposes of securitization. For example, once an HCT financing loan portfolio has been created (with "sufficiency" defined, for example, in terms of the risk profile and diversity of the borrowers, the diversity of GCTs covered, the diversity of GCT manufacturers, in addition to other metrics), the lender (or its designated party, or another party) can bundle these loans for the purposes of securitization and distribution to the broader financial markets. For example, the securitization basket may comprise 200-300 HCT financing loans with a notional value of 300 MM-500 MM USD. Credit rating, average coupon, position sizing, and the like, can be determined at the time of creation. Tranching of the loan cash flows can be determined during the creation of the securitization and subject to various market conditions that would affect the attractiveness of the securities to the market. Loans associated with multiple GCTs, various payer types, differing loan tenors, and the like, may be ideal to achieve the maximum diversification benefit from the total portfolio and to reduce the risk profile of both the overall loan basket as well as the individual tranches.

Software, Computer System, and Network Environment

Certain embodiments described herein make use of computer algorithms in the form of software instructions executed by a computer processor. In certain embodiments, the software instructions include a machine learning module, also referred to herein as artificial intelligence software. As used herein, a machine learning module refers to a computer implemented process (e.g., a software function) that implements one or more specific machine learning algorithms, such as an artificial neural network (ANN), random forest, decision trees, support vector machines, and the like, in order to determine, for a given input, one or more output values. In certain embodiments, the input comprises alphanumeric data which can include numbers, words, phrases, or lengthier strings, for example. In certain embodiments, the one or more output values comprise values representing numeric values, words, phrases, or other alphanumeric strings. In certain embodiments, the one or more output values comprise an identification of one or more response strings (e.g., selected from a database).

For example, a machine learning module may receive as input a textual string (e.g., entered by a human user, for example) and generate various outputs. For example, the machine learning module may automatically analyze the input alphanumeric string(s) to determine output values classifying a content of the text (e.g., an intent), e.g., as in natural language understanding (NLU). In certain embodiments, a textual string is analyzed to generate and/or retrieve an output alphanumeric string. For example, a machine learning module may be (or include) natural language processing (NLP) software. Examples of NLP software include, without limitation, BERT (Bidirectional Encoder Representations from Transformers), Question Answer software (e.g., IR-based factoid Question Answering, knowledge-based Question Answering, and multiple source Question Answering (e.g., IBM's Watson). In certain embodiments, machine learning modules for NLP are trained using datasets such as Stanford Question Answering Dataset (SQuAD), WikiQA dataset, TREC-QA dataset, NewsQA dataset.

In certain embodiments, machine learning modules implementing machine learning techniques are trained, for example using datasets that include categories of data described herein. Such training may be used to determine various parameters of machine learning algorithms implemented by a machine learning module, such as weights associated with layers in neural networks. In certain embodiments, once a machine learning module is trained, e.g., to accomplish a specific task such as identifying certain response strings, values of determined parameters are fixed and the (e.g., unchanging, static) machine learning module is used to process new data (e.g., different from the training data) and accomplish its trained task without further updates to its parameters (e.g., the machine learning module does not receive feedback and/or updates). In certain embodiments, machine learning modules may receive feedback, e.g., based on user review of accuracy, and such feedback may be used as additional training data, to dynamically update the machine learning module. In certain embodiments, two or more machine learning modules may be combined and implemented as a single module and/or a single software application. In certain embodiments, two or more machine learning modules may also be implemented separately, e.g., as separate software applications. A machine learning module may be software and/or hardware. For example, a machine learning module may be implemented entirely as software, or certain functions of a ANN module may be carried out via specialized hardware (e.g., via an application specific integrated circuit (ASIC)).

As shown in FIG. 4, an implementation of a network environment 400 for use in providing systems, methods, and architectures as described herein is shown and described. In brief overview, referring now to FIG. 4, a block diagram of an exemplary cloud computing environment 400 is shown and described. The cloud computing environment 400 may include one or more resource providers 402*a*, 402*b*, 402*c* (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, certain modules described herein can be separated, combined or incorporated into single or combined modules. Any modules depicted in the figures are not intended to limit the systems described herein to the software architectures shown therein.

Figure 6:
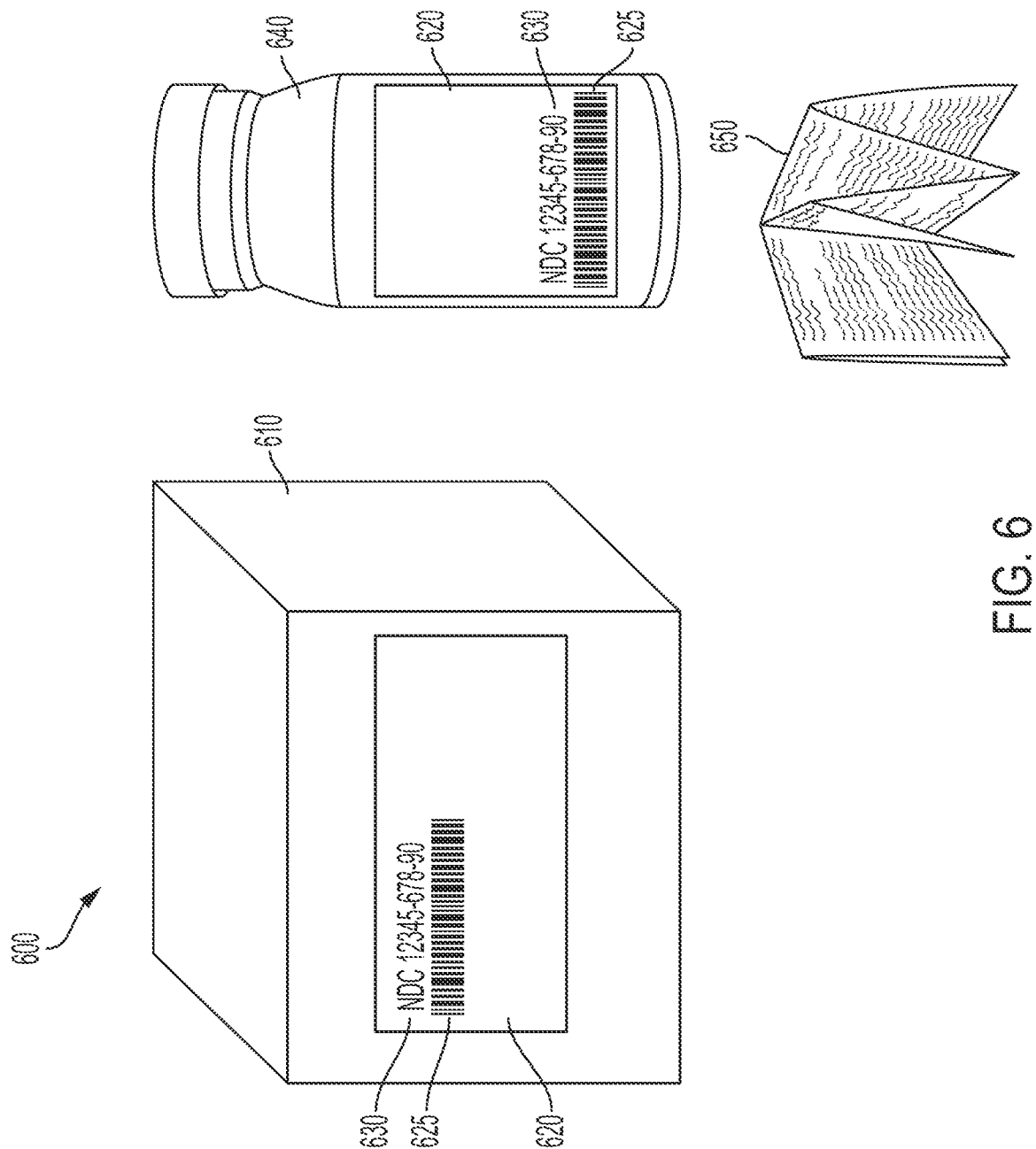
FIG. 6 is a schematic of a packaged pharmaceutical composition, according to an illustrative embodiment.

FIG. 6 illustrates a packaged pharmaceutical composition or kit 600, according to various aspects of the present embodiments. The kit 600 may include packaging 610 which may include a label 620 that displays a bar code 625 and/or a National Drug Code (NDC) 630. The kit 600 may also include a vessel 640 for containing the drug/pharmaceutical composition. The vessel 640 may also include a label 620 that displays a bar code 625 and/or a National Drug Code (NDC) 630. The kit 600 may also include an insert 650 with information about the drug/pharmaceutical composition. Alternatively, or in addition, the insert 650 may include a description indicating how the drug is financed. For example, in certain embodiments, the insert 650 includes a description indicating the drug is financed according to any of the HCT financing embodiments described herein. In some embodiments, the insert 650 may include one or more folded pieces of paper with information written thereon (for example, one side or on both sides). In some embodiments, the insert 650 may be disposed within the packaging 610. In some embodiments, the insert 650 may be wrapped around the vessel 640 (for example, in embodiments in which the vessel 640 is substantially cylindrical). In some embodiments, the insert 650 may be attached to the side of the vessel 640 (for example, in embodiment in which the vessel 640 has a substantially square or rectangular cross section). In some embodiments, the insert may be disposed between the label 620 and the vessel 640 and/or packaging 610 (i.e., "behind" the label 620). The vessel 640 may be or include a pharmaceutically acceptable vessel. The vessel 640 may be sealed or secured in accordance with industry-accepted practices and protocols. In certain embodiments, the insert 650 is displayed via a website or other computer accessible network.

Constructive Example—The following is an Example Term Sheet for an instrument (e.g., loan) that is part of a high cost therapy (HCT) financing, according to certain embodiments described herein.

Form of

Summary of Indicative Terms and Conditions
CTxO Loan

[The terms and conditions summarized in this term sheet are provided for discussion purposes only and do not constitute an offer, agreement, or commitment. The terms and conditions contained herein are subject to the satisfactory review and execution of documentation. The parties agree and acknowledge that this Summary of Indicative Terms and Conditions constitutes a non-binding letter of intention and obligates neither party to proceed with or consummate the transaction described herein. Except as provided in the next sentence, this Summary of Indicative Terms and Conditions does not and is not intended to create any legal obligation or enforceable right in any party.

The parties hereto acknowledge that "CTxO" and the related term, "CRxO," are trademarked. Furthermore, the loan structure contained herein, as well as anything derived from its concepts, are claimed as trade secrets of Octaviant Financial, Inc., subject to non-disclosure agreements, are patent protected and copyrighted.]

| | |
|---|---|
| Borrower: | _____, a _____ [(the "Borrower")], which is the payer (the "Payer") of the HCT (as defined below). |
| HCT Beneficiary: | _____, an individual residing in _____ (the "Beneficiary"), who is the recipient of the HCT, and is [the individual policyholder] [an insured under the policy held by _____, the policyholder, and] offered by the Payer. |
| Guarantor: | All obligations of the Borrower with respect to the Facilities (as defined below) are to be unconditionally guaranteed (the "Guaranty") [(as to payment, rather than collection)] by _____, a _____ (the "Guarantor"), which is the employer of the policyholder and offers health insurance coverage for the Beneficiary at the commencement of the Episode of Care (as defined below). |
| Loan Servicer: | Octaviant Financial, Inc. or its affiliate (in such capacity, the "Loan Servicer"). |
| Lender[s]: | Octaviant Financial, Inc. or its affiliate (in such capacity, the "[Senior] Lender")[, and the Manufacturer (as defined below) (the Manufacturer, together with the Senior Lender, the "Lenders")]. |

| | |
|---|---|
| Benefits Administrator: | _____, as benefits administrator (the "OBA"). |
| Facilities: | (i) Senior unsecured term loan in the original principal amount of $_____¹ (the "Upfront Draw"); and<br>(ii) Senior unsecured term loan in the original principal amount of $_____² (the "Second Draw") and together with the Upfront Draw, the "Facilities"). |
| [Holdback: | The Borrower shall benefit from the deferral of payment [to the Manufacturer] of an amount equal to [10]% of the HCT Price (the "Holdback Amount"), which amount, including any associated interest, shall not be payable by the Borrower until the later of (a) the Facilities have been paid in full and terminated or (b) the end of the Episode of Care and shall reduce the amount required to be drawn under the Second Draw.<br>The Credit Documents shall include an agreement (the "Holdback Subordination") by the Manufacturer that the Holdback Amount is subordinated to the payment in full of the obligations owed to the Senior Lender.] |
| Interest Rate: | Interest will be due and payable on the outstanding balance of the Facilities at an interest rate equal to [[Term SOFR/Daily Simple SOFR] plus [spread]]³ plus _____% per annum (the "Interest Rate").<br>[Need to add for Holdback.] |
| Arrangement Fee: | An arrangement fee in an amount equal to [1.0]% of the sum of (i) the original principal amount of the Upfront Draw plus (ii) the original principal amount of the Second Draw shall be paid to the Loan Servicer for its own account, in its capacity as arranger, on the Closing Date. |
| Servicing Fee: | A quarterly fee in an amount equal to $_____,⁴ which fee shall be payable to the Loan Servicer for its own account, quarterly in advance commencing on the Closing Date. |
| OBA Fee: | A [quarterly] fee in an amount equal to $_____ (the "OBA Fee"), [which fee shall be due to and earned by the OBA,] and payable by the Borrower to the Loan Servicer for the account of the OBA, quarterly in advance commencing on the Closing Date. The OBA Fee anticipated to be paid as part of the Upfront Draw is the "Initial OBA Fee." |
| [VBA Premium Payment: | A non-refundable value-based agreement (a "VBA") premium in the amount of $_____ (the "VBA Premium") shall be due and payable by or on behalf of the Borrower to the Manufacturer on the Closing Date from proceeds of the Upfront Draw.] |
| Default Rate: | The default interest rate will be the then-applicable Interest Rate plus two percent (2%) per annum. |
| Late Charge: | Five percent (5%) of the amount of any payment of principal, interest or fee that is past due fifteen (15) days or more. |
| Availability: | The Upfront Draw will be available in a single draw on the date (the "Closing Date")[that is at least two business days following the date] on which definitive credit documentation for the Facilities (the "Credit Documents") is executed and delivered by each of the parties thereto, subject to full and complete satisfaction by the Borrower and the Guarantor of the conditions precedent set forth therein.<br>The Second Draw will be available in a single draw on any business day (the "Second Draw Funding Date")[that is at least two business days] after the date (the "Determination Date") that a determination is made as to whether or not the HCT is Indicatively Efficacious or non-Indicatively Efficacious (as such term will be defined in the Credit Documents) with respect to the Beneficiary, but no more than [ ] days after the Determination Date; provided that, the Second Draw will only be available if the HCT is determined to be Indicatively Efficacious. Amounts repaid under the Facilities may not be reborrowed. |
| Permitted Purposes: | The Borrower shall use the proceeds of the Upfront Draw only to fund: (a) a portion of the total cost (the "HCT Price") of _____⁵ (the "HCT") manufactured by _____ (the "Manufacturer") and made available to the Beneficiary by _____ (the "Provider") pursuant to a medical prescription for the HCT written on _____ (such date, the "Prescription Date"); (b) Procedure-Related Costs (as such term will be defined in the Credit Documents); (c) the Initial OBA Fee; (d) Bundled Expenses (as defined below); (e) any fees or expenses of the Facility, including the Arrangement Fee [and (f) the VBA Premium].<br>The Borrower shall use the proceeds of the Second Draw only to fund (a) the remainder of the HCT Price not paid by proceeds of the Upfront Draw less the Holdback Amount; (b) an estimate of the post-therapeutic Bundled Expenses; and (c) the anticipated aggregate OBA Fee to be paid during the Episode of Care (as defined below) minus the Initial OBA Fee. |

| | |
|---|---|
| | "Bundled Expenses" means the costs and expenses of pre- or post-therapy therapeutic treatments and services as prescribed or recommended by one or more of the OBA, the Provider or any of the Beneficiary's subsequent treating providers or the Manufacturer, or as otherwise approved by the OBA, for monitoring, analysis and supporting medical care incurred or expected to be incurred (as approved in writing by the OBA) during the Episode of Care (collectively, but excluding any Procedure-Related Costs) related to the medical condition of the Beneficiary necessitating the HCT. "Episode of Care" means all services provided to the Beneficiary to treat the medical condition, including the HCT, Procedure-Related Costs and Bundled Expenses, beginning on the Prescription Date and ending on the Maturity Date. The Beneficiary's underlying medical condition necessarily continues during the treatment with the HCT and throughout the period during which Procedure-Related Costs and Bundled Expenses are incurred for the duration of the Episode of Care (the "Pre-Existing Condition"). |
| Maturity: | The Facilities shall mature on the [fourth/fifth] anniversary of the Closing Date (the "Maturity Date"). |
| Amortization: | The Borrower shall make quarterly principal payments on the Facilities in an amount equal to [___]% of the aggregate original principal amount of the Facilities borrowed on each Funding Date (and recalculated on each Funding Date), commencing with the first day of the first full fiscal quarter following the Closing Date and on the first day of each fiscal quarter thereafter prior to the Maturity Date. |
| Interest Payments: | The Borrower shall make quarterly payments of accrued interest on the outstanding and unpaid principal amount of the Facilities, commencing with the first day of the first full fiscal quarter following the Closing Date and on the first day of each fiscal quarter thereafter prior to the Maturity Date. Unless sooner paid in full, the outstanding principal amount of the Facilities and all then-accrued and unpaid interest thereon shall be due and payable on the Maturity Date. |
| Mandatory Prepayment: | If on any date the HCT is determined to be non-Efficacious (as such term will be defined in the Credit Documents), the outstanding principal amount of the Facilities and all then-accrued and unpaid interest thereon shall be immediately due and payable along with any applicable prepayment penalties.$^6$ [The Borrower shall immediately prepay, or cause to be prepaid, the Facilities in an aggregate principal amount equal to 100% of any cash proceeds the Borrower receives pursuant to the VBA.] At any time after the second anniversary of the Closing Date, the Borrow may voluntarily prepay the outstanding balance of the Facilities [(in whole but not in part)]. For any prepayment, the Borrower shall pay to the Loan Servicer for the account of the Lender[s] on the date of prepayment a prepayment premium equal to: for mandatory prepayments on or prior to the second anniversary of the Closing Date, 4.0% of the principal amount of such prepayment; for any prepayments after the second anniversary of the Closing Date, 3.0% of the principal amount of such prepayment; and for any prepayments after the third anniversary of the Closing Date, 1.0% of the principal amount of such prepayment. If such prepayment occurs within the first twenty-four (24) months from closing, 4%; if the prepayment occurs within the subsequent twelve (12) months, 3%, if the prepayment occurs subsequently, 1%. [Add language that Holdback doesn't get paid back if determined non-efficacious after the Determination Date.] |
| Credit Documents: | The Credit Documents for the Facilities will include a "payment plan agreement" (i.e., loan agreement), a promissory note, a guaranty agreement by the Guarantor, [the VBA,] [the Holdback Subordination,] and other credit documents, in each case satisfactory to the Loan Servicer in form and substance. The Credit Documents will contain the terms and conditions described herein and other customary provisions satisfactory to the Loan Servicer. |
| Conditions Precedent: | The funding of the Upfront Draw on the Closing Date will be conditioned upon satisfaction on or before the Closing Date of customary closing conditions, including, without limitation, full execution and delivery of the Credit Documents; accuracy of representations and warranties made by the Borrower and the Guarantor; absence of defaults; delivery of evidence of authority; payment of fees and expenses; and satisfaction of other customary corporate and document delivery requirements. The obligation of the Lender[s] to make the Facilities available to the Borrower on any Funding Date will be conditioned upon satisfaction on or before such Funding Date of customary funding conditions, including, without limitation, delivery of a notice of borrowing; accuracy of representations and warranties made by the Borrower and the Guarantor; and absence of defaults. |

| | |
|---|---|
| Representations and Warranties: | Customary for commercial loans (to apply to the Borrower and to the Guarantor), including, but not limited to: formation and organization; power and authority; enforceability; governmental approvals; absence of conflicts; compliance with laws and agreements; accuracy of disclosure; solvency; use of proceeds; and inapplicability of the Investment Company Act of 1940, as amended. |
| Affirmative Covenants: | Customary for commercial loans (to apply to the Borrower and to the Guarantor), including, but not limited to, covenants regarding the following matters: notification of defaults and other significant events; maintenance of existence; and compliance with laws and other legal requirements. |
| Negative Covenants: | Customary for commercial loans (to apply to the Borrower and to the Guarantor), including, but not limited to, covenants regarding limitations on the following matters: changes in identity or organizational matters; changes in nature of business; limitations on mergers and other fundamental changes; restrictive subsidiary agreements; and use of loan proceeds. |
| Events of Default: | Customary for commercial loans, including, but not limited to: nonpayment of principal, interest and other required amounts; breach of representation or warranty; breach of covenant; failure of any Credit Document to be in full force and effect; bankruptcy and insolvency events; material adverse change; merger or consolidation; termination, dissolution, or liquidation; and change of control. |
| Remedies: | Customary for commercial loans. |
| Withholding Taxes: | The Borrower will indemnify the Lender[s] against withholding taxes on payments under the Facilities (as well as against documentary and similar taxes). |
| Assignments: | The Borrower may not assign its rights or obligations under the Facilities without the prior written consent of the Loan Servicer; provided, that, without the consent of the Loan Servicer, the Borrower shall make such assignment to another Payer (a "Subsequent Payer"), as a Pre-Existing Condition of the Beneficiary, if the Beneficiary becomes an individual policyholder or an insured under a policy held by a policyholder and offered by such Subsequent Payer. The original Borrower making such assignment will pay to the Loan Servicer, for application to the Facilities on the next quarterly payment date, an amount equal to all accrued and unpaid amortization and interest on the Facilities calculated as of the date of such assignment; provided that, notwithstanding the foregoing, the original Borrower and Guarantor shall not be released from liability for payments under the facilities. The [Senior] Lender will be permitted to assign the Facilities and its commitment to make loans under any of the Facilities. [The Manufacturer may not assign its rights or obligations under the Facilities.] |
| Expenses and Indemnification: | The Borrower (including any subsequent Payer that becomes the Borrower) will pay (a) all out-of-pocket expenses of the Loan Servicer associated with the preparation, execution, delivery and administration of the credit documentation and any amendments or waivers with respect thereto (including the fees, charges and disbursements of the Loan Servicer's counsel) and (b) all out-of-pocket expenses of the Loan Servicer (including the fees, charges and disbursements of the Loan Servicer's counsel) in connection with the enforcement of the credit documentation. The Loan Servicer, the Lender[s], the OBA and each of their respective affiliates (and their respective officers, directors, employees, advisors and agents) will have no liability for, and will be indemnified by the Borrower (including any subsequent Payer that becomes the Borrower) and held harmless against, any loss, liability, cost or expense incurred in respect of or relating to the financing contemplated hereby, the use or the proposed use of proceeds thereof, any failure of the HCT to perform as expected including whether or not the HCT is Indicatively Efficacious or Efficacious, any adverse effect or adverse event including any medical professional liability or product liability with respect to the HCT and any Procedure-Related Costs and Bundled Expenses, any obligation to provide the HCT or the Bundled Expenses or any other medial product or service, any actual or alleged violation of law by any individual or entity by any governmental agency or authority arising from or relating to the HCT or any payment or funding thereof, and any claim, litigation, investigation or proceeding relating to any of the foregoing (except to the extent determined by a final, nonappealable judgment of a court of competent jurisdiction to have resulted from the gross negligence or willful misconduct of the indemnified party). |

| | |
|---|---|
| Waiver of Jury Trial: | The credit documentation will include mutual waivers of jury trial. |
| Governing Law: | New York. |

[1] To be an amount equal to the sum of (i) [77]% of the HCT Price plus (ii) Procedure-Related Costs plus (iii) the Initial OBA Fee [plus (iv) the VBA Premium] plus (v) pre-therapeutic Bundled Expenses (as defined below) that have been approved in writing by the OBA plus (vi) the Arrangement Fee.
[2] To be an amount equal to (i) (a) [23]% of the HCT Price minus (b) the Holdback Amount plus (ii) an estimate of the post-therapeutic Bundled Expenses approved in writing by the OBA plus (iii) (c) the anticipated aggregate OBA Fee to be paid during the Episode of Care minus (d) the Initial OBA Fee.
[3] Draft note: To be updated as market settles on LIBOR replacement.
[4] To be [__]% of the sum of (i) the original principal amount of the Upfront Draw plus (ii) the original principal amount of the Second Draw.
[5] Describe applicable high-cost therapy.
[6] Note: would include reasonable period to trigger warranty, etc.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A packaged pharmaceutical composition or kit comprising a pharmaceutically acceptable vessel, a therapeutic agent secured or otherwise sealed within the vessel, and a label, wherein the therapeutic agent comprises a high cost therapy drug (a HCT drug), and the label comprises a description and/or code that identifies how the HCT drug is financed.

2. The packaged pharmaceutical composition of claim 1, wherein the description on the label indicates that said HCT financing comprises an upfront draw paid to a party that provides and/or administers the HCT to the HCT beneficiary and is made at or near the time of administration of the HCT to the HCT beneficiary.

3. The packaged pharmaceutical composition of claim 1, wherein the drug is a gene or cell therapy drug (GCT drug).

4. The packaged pharmaceutical composition of claim 1, wherein the drug is a single or finite dose gene and/or cellular therapy.

5. The packaged pharmaceutical composition of claim 1, wherein the drug comprises one or more members selected from the group consisting of: a biologic drug, a small molecule drug, a gene therapy, and a cell therapy.

6. The packaged pharmaceutical composition of claim 5, wherein the drug comprises an excipient or other pharmaceutically acceptable carrier.

7. The packaged pharmaceutical composition of claim 1, wherein the pharmaceutically acceptable vessel contains a unit dose of the therapeutic agent.

8. The packaged pharmaceutical composition of claim 1, wherein the description on the label indicates that said HCT financing comprises a premium payment for a value based agreement (VBA) structured as a performance guaranty of initial efficacy of the HCT for the HCT beneficiary.

9. The packaged pharmaceutical composition of claim 2, wherein the description on the label indicates that said HCT financing comprises a second draw paid within an agreed-upon period of time after administration of the HCT and upon determination of initial efficacy of the HCT for the HCT beneficiary.

10. The packaged pharmaceutical composition of claim 1, wherein the description on the label indicates that said HCT financing comprises bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary, said bundled expenses being compensated for a contractually-defined episode of care, wherein said episode of care is a time period associated with the HCT for which a bundled payment is made.

11. The packaged pharmaceutical composition of claim 1, wherein the description on the label indicates that:
said HCT financing comprises a multi-year structured loan having a tenor that ends contiguously with a defined episode of care, wherein said episode of care is contractually defined to establish a pre-existing condition of the HCT beneficiary, thereby facilitating portability and/or transferability of associated liability from the borrower to another party while the HCT beneficiary is considered to have the pre-existing condition.

12. The packaged pharmaceutical composition of claim 1, wherein the description on the label indicates that:
said HCT financing comprises a value based agreement having a period that ends contiguously with a defined episode of care, wherein said episode of care is contractually defined to establish a pre-existing condition of the HCT beneficiary, thereby facilitating portability and/or transferability of associated liability while the HCT beneficiary is considered to have the pre-existing condition.

13. The packaged pharmaceutical composition of claim 1, wherein the description on the label indicates that one or more of (i) to (vi) is applicable to said HCT financing, as follows:

(i) said HCT financing comprises an upfront draw paid to a party that provides and/or administers the HCT to the HCT beneficiary and is made at or near the time of administration of the HCT to the HCT beneficiary;

(ii) said HCT financing comprises a premium payment for a value based agreement (VBA) structured as a performance guaranty of initial efficacy of the HCT for the HCT beneficiary;

(iii) said HCT financing comprises a second draw paid within an agreed-upon period of time after administration of the HCT and upon determination of initial efficacy of the HCT for the HCT beneficiary;

(iv) said HCT financing comprises bundled expenses for pre- and/or post-therapy therapeutic treatments and/or services rendered to the HCT beneficiary related to an underlying medical condition of the HCT beneficiary addressed by the HCT, and/or monitoring and/or analysis of the efficacy of the HCT administered to the HCT beneficiary, said bundled expenses being compensated for a contractually-defined episode of care, wherein said episode of care is a time period associated with the HCT for which a bundled payment is made;

(v) said HCT financing comprises a multi-year structured loan having a tenor that ends contiguously with a defined episode of care, wherein said episode of care is contractually defined to establish a pre-existing condition of the HCT beneficiary, thereby facilitating portability and/or transferability of associated liability from the borrower to another party while the HCT beneficiary is considered to have the pre-existing condition; and (vi) said HCT financing comprises a value based agreement having a period that ends contiguously with a defined episode of care, wherein said episode of care is contractually defined to establish a pre-existing condition of the HCT beneficiary, thereby facilitating portability and/or transferability of associated liability while the HCT beneficiary is considered to have the pre-existing condition.

\* \* \* \* \*

UNITED STATES PATENT AND TRADEMARK OFFICE
CERTIFICATE OF CORRECTION

| | | |
|---|---|---|
| PATENT NO. | : 11,288,738 B1 | Page 1 of 1 |
| APPLICATION NO. | : 17/327604 | |
| DATED | : March 29, 2022 | |
| INVENTOR(S) | : Emad Samad et al. | |

It is certified that error appears in the above-identified patent and that said Letters Patent is hereby corrected as shown below:

On the Title Page

Item [73], delete "Octavian! Financial, Inc." insert --Octaviant Financial, Inc.--

Signed and Sealed this
Tenth Day of May, 2022

Katherine Kelly Vidal
*Director of the United States Patent and Trademark Office*